US010266569B2

(12) United States Patent
Volchkov et al.

(10) Patent No.: US 10,266,569 B2
(45) Date of Patent: Apr. 23, 2019

(54) PEPTIDES INCLUDING A BINDING DOMAIN OF THE VIRAL PHOSPHOPROTEIN (P) SUBUNIT TO THE VIRAL RNA FREE NUCLEOPROTEIN ($N^0$)

(71) Applicants: INSTITUT NATIONAL DE LA SANTÉ ET DE LA RECHERCHE MÉDICALE (INSERM), Paris (FR); CENTRE NATIONAL DE LA RECHERCHE SCIENTIFIQUE (CNRS), Paris (FR); UNIVERSITÉ CLAUDE BERNARD—LYON 1, Villeurbanne (FR); ECOLE NORMALE SUPÉRIEURE DE LYON (ENS DE LYON), Lyons (FR); UNIVERSITÉ GRENOBLE ALPES, Saint-Martin-d'Hères (FR)

(72) Inventors: Viktor Volchkov, Lyons (FR); Marc Jamin, Grenoble (FR); Philip Lawrence, Lyons (FR); Filip Yabukarski, Stanford, CA (US)

(73) Assignees: INSERM (Institut National de la Sante et de la Recherche Medicale), Paris (FR); Centre National de le Recherche Scientifique (CNRS), Paris (FR); Université Claude Bernard—Lyon 1, Villeurbanne (FR); Ecole Normale Superieure de Lyon (ENS de Lyon), Lyons (FR); Université Grenobles Alpes, Saint-Martin-d'Heres (FR)

( * ) Notice: Subject to any disclaimer, the term of this patent is extended or adjusted under 35 U.S.C. 154(b) by 0 days.

(21) Appl. No.: 15/325,599

(22) PCT Filed: Jul. 17, 2015

(86) PCT No.: PCT/EP2015/066419
§ 371 (c)(1),
(2) Date: Jan. 11, 2017

(87) PCT Pub. No.: WO2016/009044
PCT Pub. Date: Jan. 21, 2016

(65) Prior Publication Data

US 2017/0158741 A1 Jun. 8, 2017

(30) Foreign Application Priority Data

Jul. 18, 2014 (EP) .................................... 14306168

(51) Int. Cl.

| | |
|---|---|
| ***A61K 38/00*** | (2006.01) |
| ***C07K 14/00*** | (2006.01) |
| ***C07K 14/005*** | (2006.01) |

(52) U.S. Cl.
CPC ............ *C07K 14/005* (2013.01); *A61K 38/00* (2013.01); *C12N 2760/18222* (2013.01); *C12N 2760/18233* (2013.01); *C12N 2760/18433* (2013.01)

(58) Field of Classification Search
CPC .................. A61K 38/00; C07K 14/005; C12N 2760/18222; C12N 2760/18233
USPC ........................... 530/300, 324, 325; 514/3.7
See application file for complete search history.

(56) References Cited

U.S. PATENT DOCUMENTS 7,803,612 B2 * 9/2010 Audonnet ........... A61K 39/155
435/320.1

FOREIGN PATENT DOCUMENTS

| | | | |
|---|---|---|---|
| WO | 2002000694 | A2 | 1/2002 |
| WO | 2005028673 | A1 | 3/2005 |
| WO | 2006115843 | A2 | 11/2006 |
| WO | 2006117456 | A1 | 11/2006 |

OTHER PUBLICATIONS

UniProt A0A1L7B8D3, pp. 1-3. Integrated into UniProtKB/TrEMBL Mar. 15, 2017.*
UniProt P06940-PHOSP, pp. 1-4. Integrated into UniProtKB/TrEMBL Jan. 1, 1988.*
UniProt E7DW56, pp. 1-2. Integrated into UniProtKB/TrEMBL Mar. 8, 2011.*
UniProt R4N1G6, pp. 1-3. Integrated into UniProtKB/TrEMBL Jul. 24, 2013.*
Karlin et al, "Detecting remote sequence homology in disordered proteins: discovery of conserved motifs in the N-termini of Mononegavirales phosphoproteins", PLOS ONE, vol. 7, No. 3, Mar. 5, 2012, pp. 1-16.
Bruhn et al, "Crystal structure of the Nipah virus phosphoprotein tetramerization domain", Journal of Virology, vol. 38, No. 1, Jan. 1, 2014, pp. 758-762.
Database UniProt, Mar. 8, 2011, accession No. E7DWI2.
Database Unitprot, Jul. 1, 1997, accession No. 011709.
Curran et al, "An N-terminal domain of the Sendai paramyxovirus p protein acts as a chaperone for the NP protein during the nascent chain assembly step of genome replication", Journal of Virology, vol. 69, No. 2, Feb. 1995, pp. 849-855.

(Continued)

*Primary Examiner* — Julie Ha
(74) *Attorney, Agent, or Firm* — W & C IP

(57) ABSTRACT

The invention related to isolated peptides including a binding domain of the viral phosphoprotein (P) subunit to the viral RNA free nucleoprotein ($N^0$) which has the property to inhibit the replication of viruses from the subfamily Paramyxovirinae (like Henipavirus, Rubulavirus or Morbillivirus). These isolated peptides may be used for the prevention or the treatment of Paramyxovirinae infection.

16 Claims, 14 Drawing Sheets

Specification includes a Sequence Listing.

(56) References Cited

OTHER PUBLICATIONS

Yabukarski et al., "Structure of Nipah virus unassembled nucleoprotein in complex with its viral chaperone", Nature Structural & Molecular Biology, vol. 21, No. 9, Sep. 2014, pp. 754-759.

* cited by examiner

Figure 1:
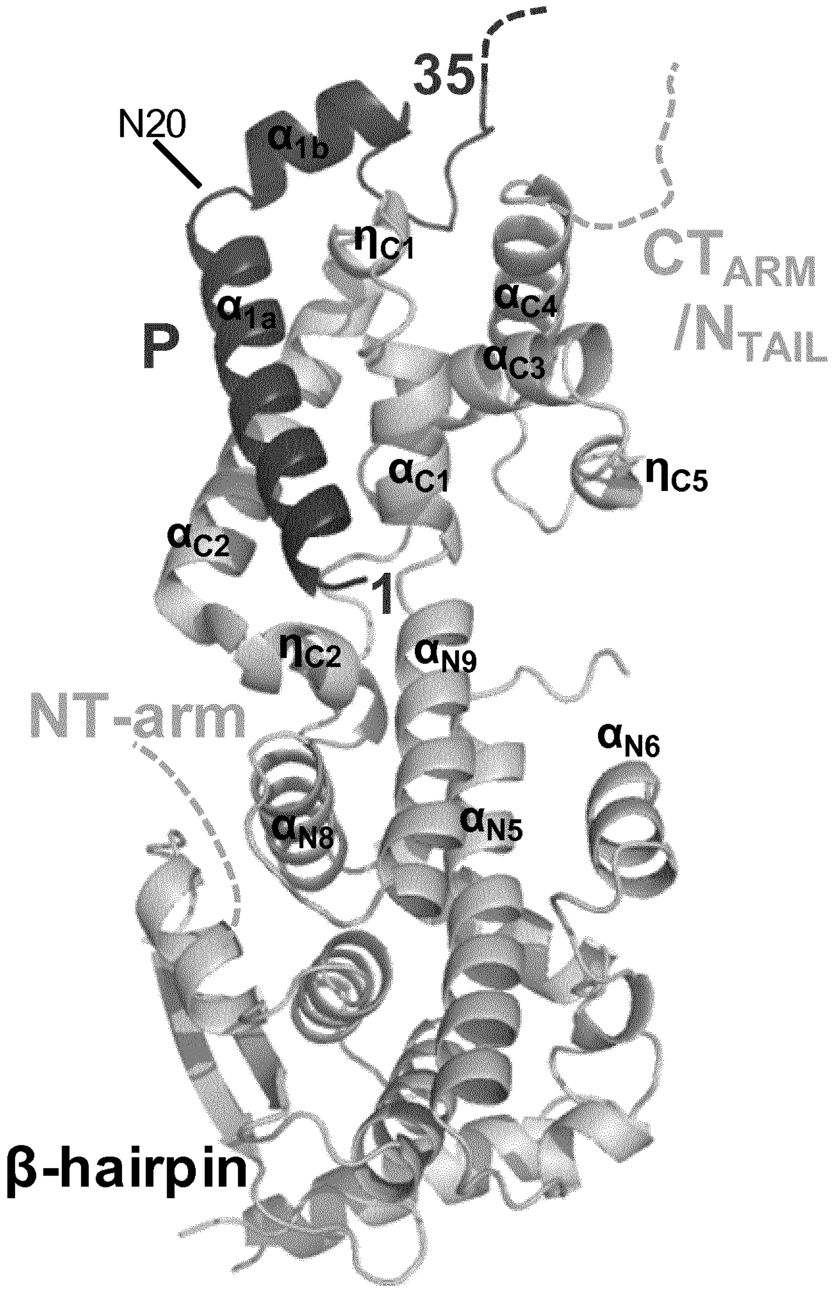

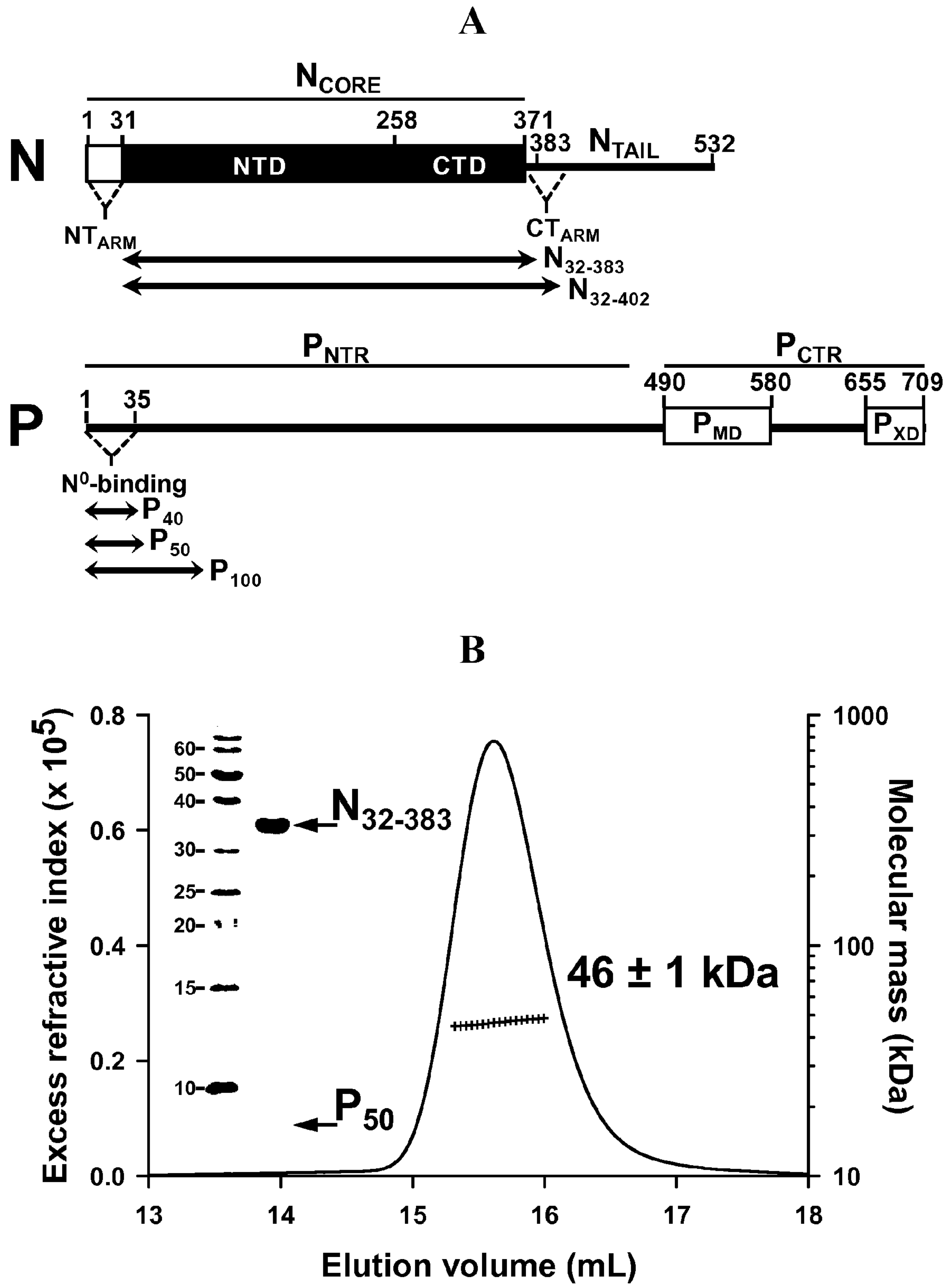
Figure 1 A and B

C
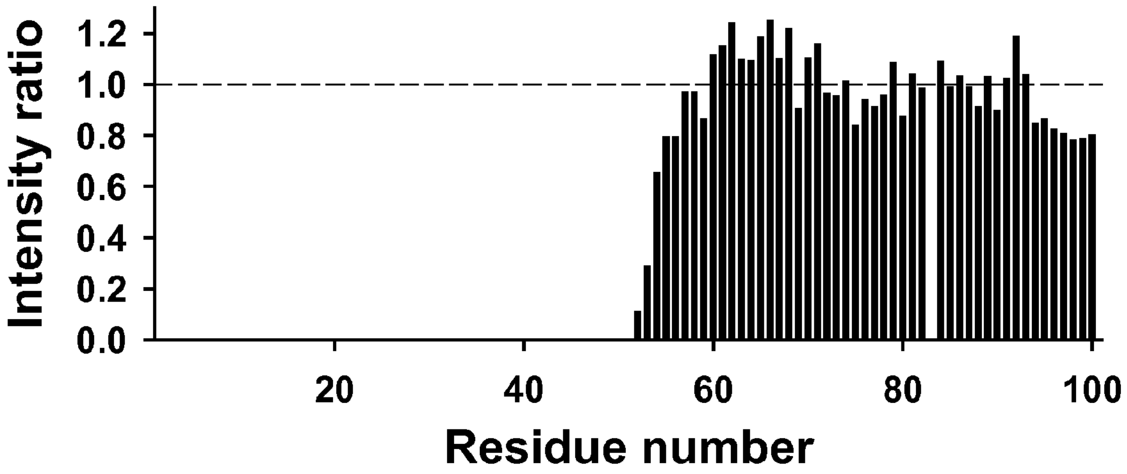
D
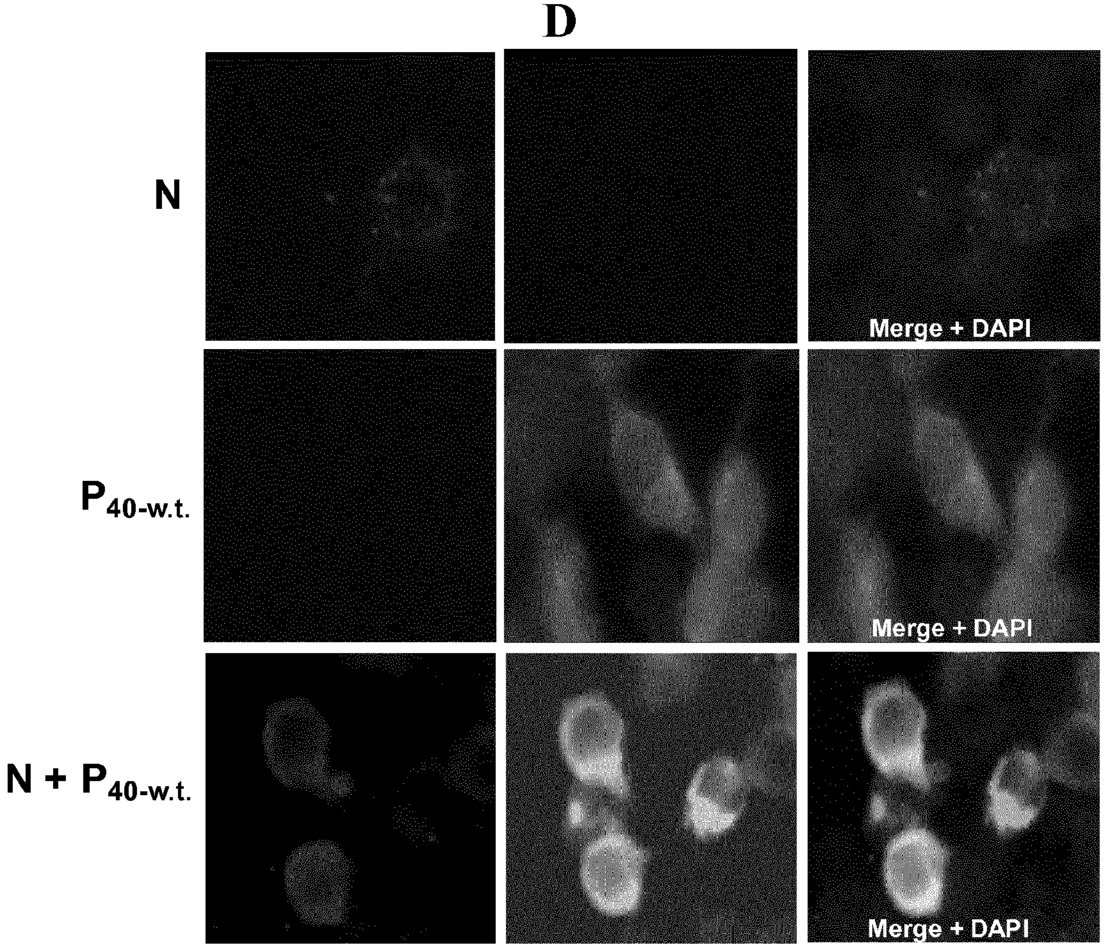
Figure 1 C and D

E

Figure 2:
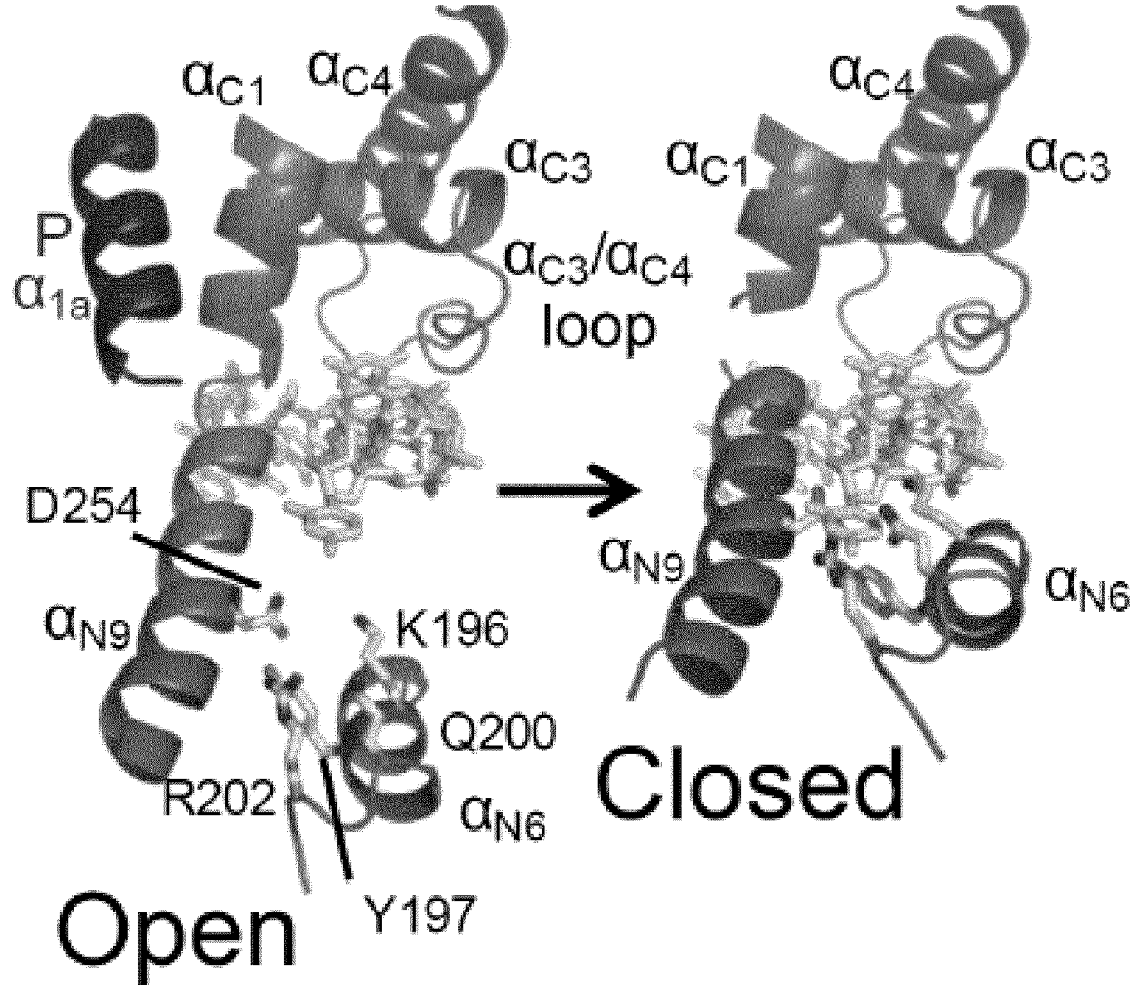

A
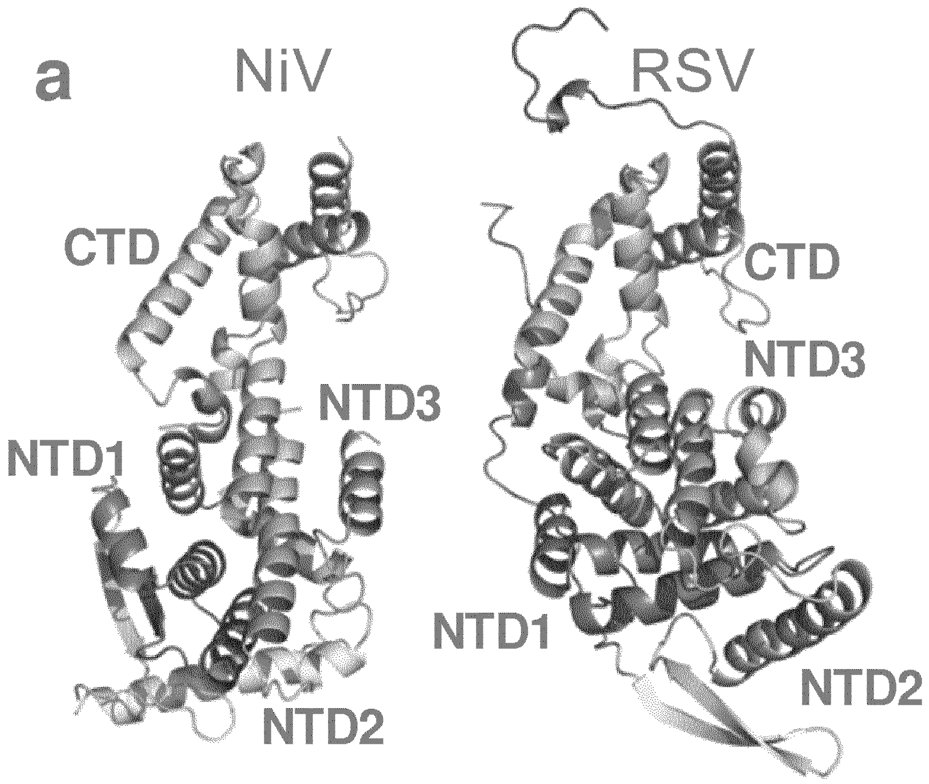
B
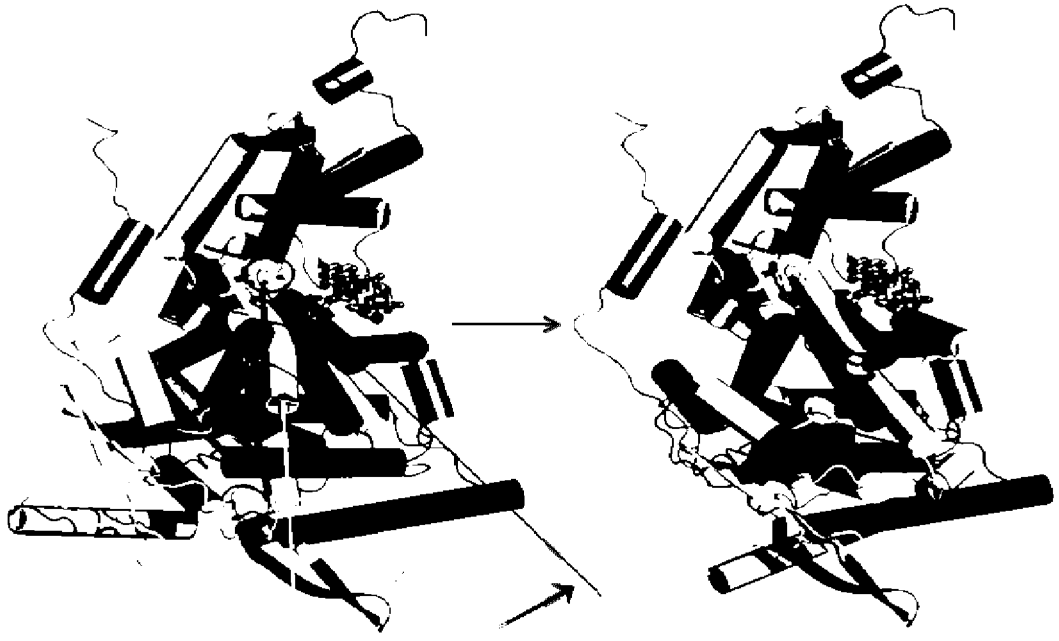
Figure 2 A and B

C
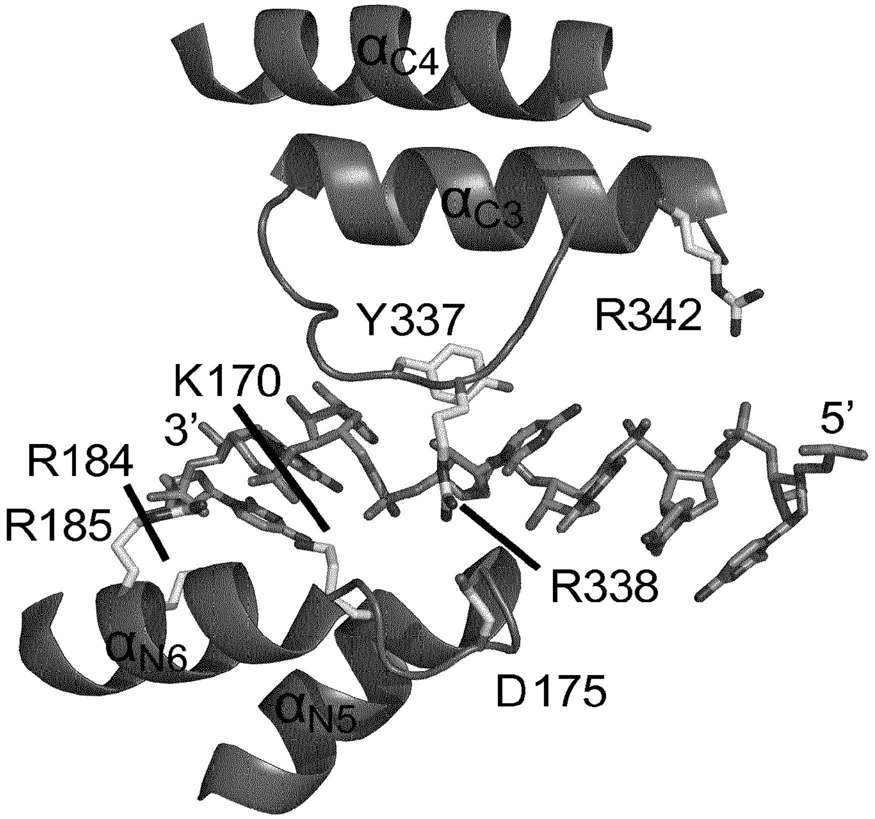
D
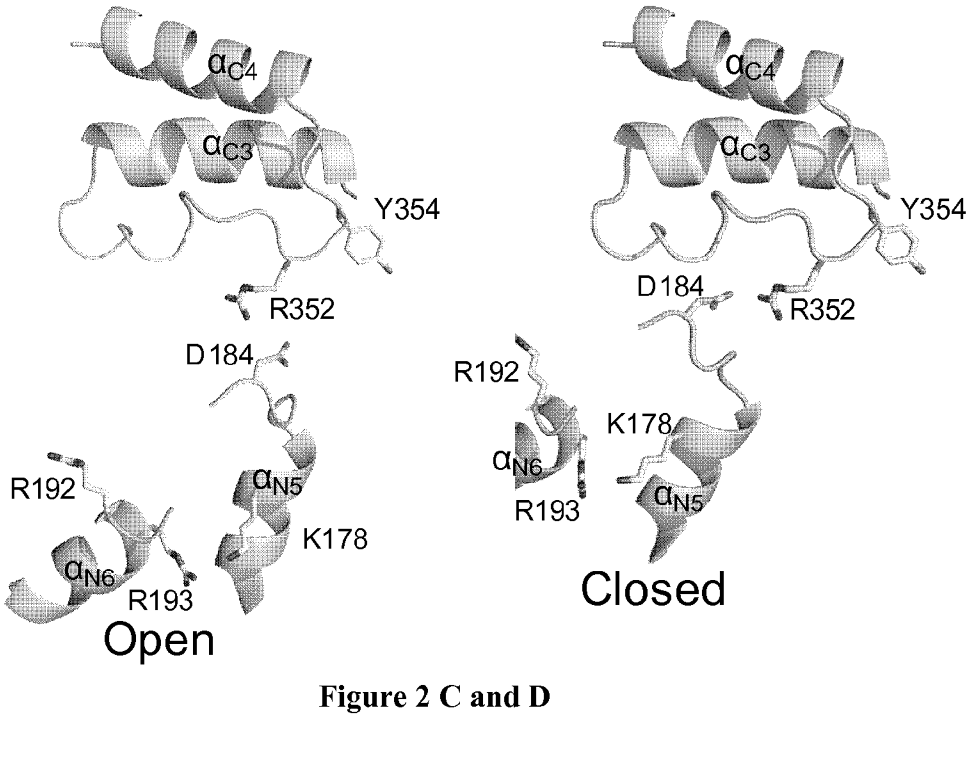
Figure 2 C and D

E
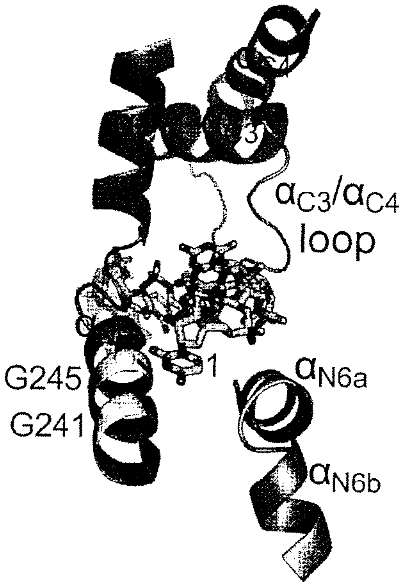
F
| | | | | |
|---|---|---|---|---|
| NiV | 189 | SETRRWAKYVQQKRVNP | 205 | SEQ ID NO: 37 |
| MeV | 191 | SELRRWIKYTQQRRVVG | 207 | SEQ ID NO: 38 |
| MuV | 191 | SADRRFAKYQQQGRLEA | 207 | SEQ ID NO: 39 |
| NDV | 189 | SETRRINKYMQQGRVQK | 205 | SEQ ID NO: 40 |
Figure 2 E and F

G

Figure 3:
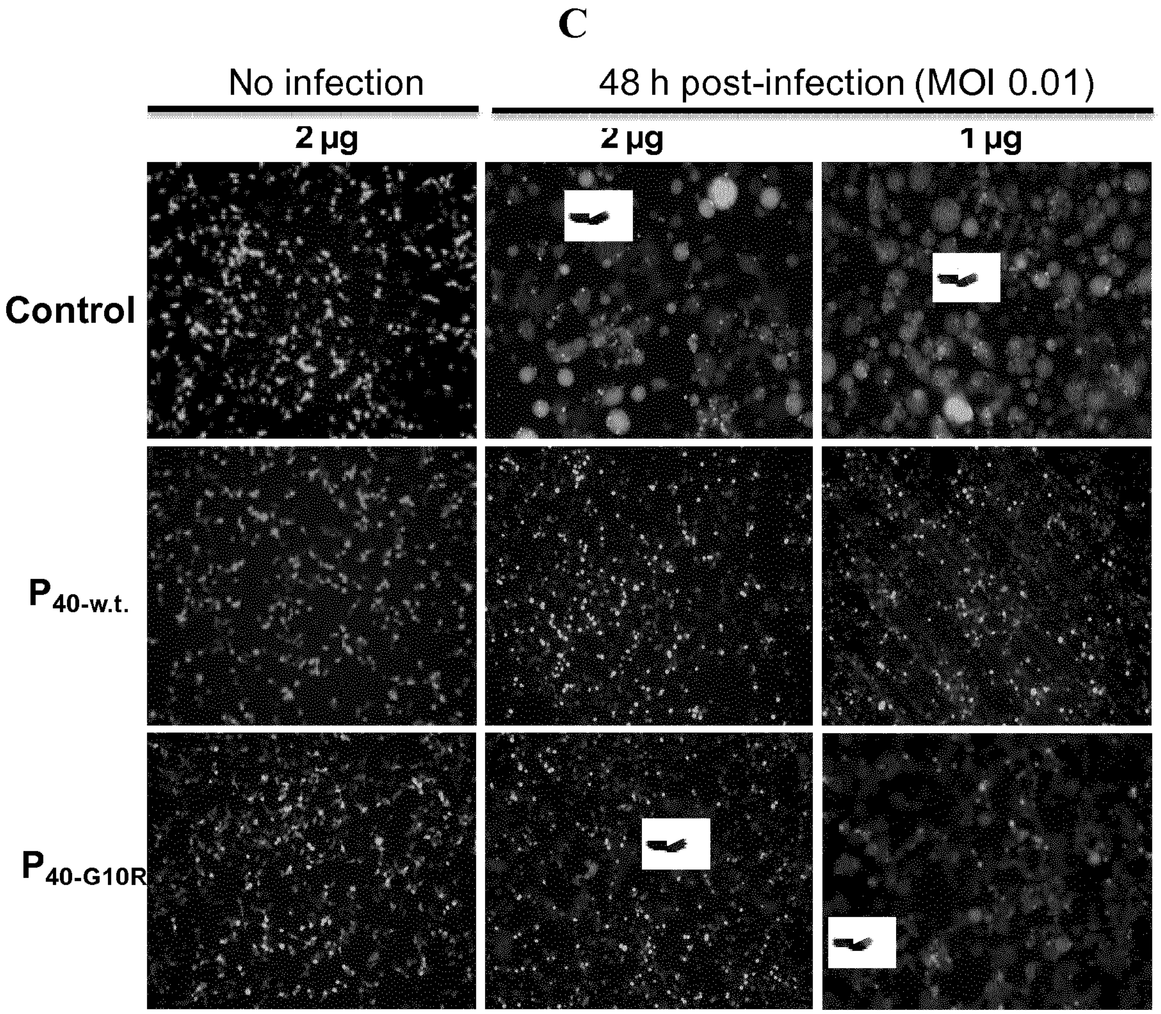

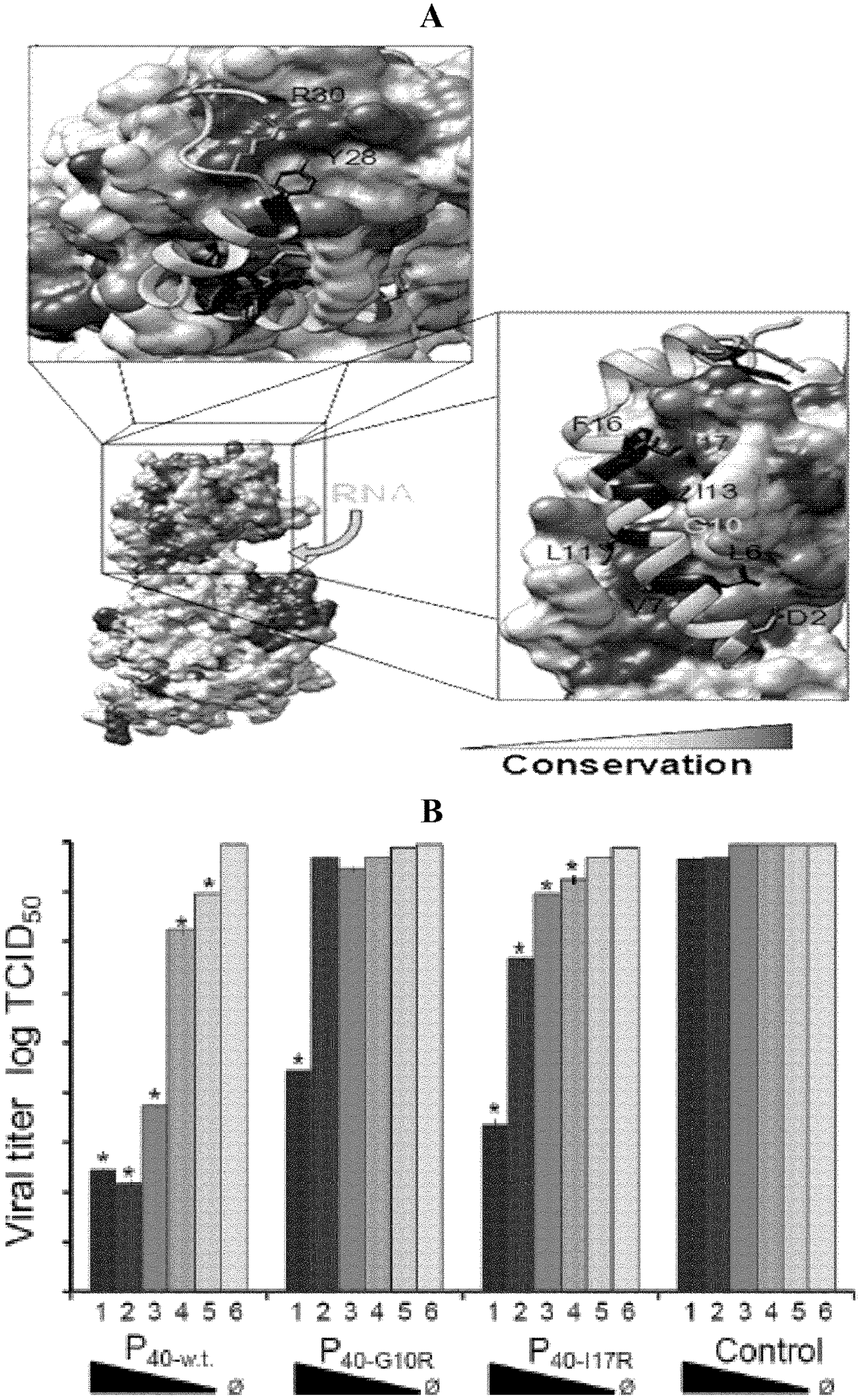
Figure 3 A and B

Figure 4:
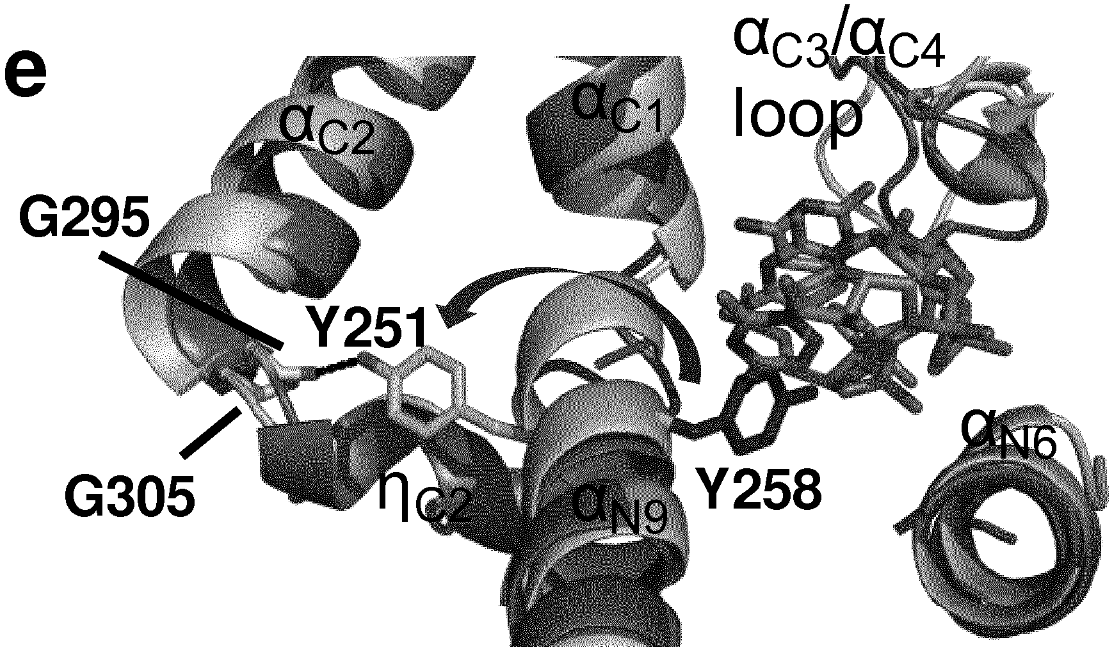

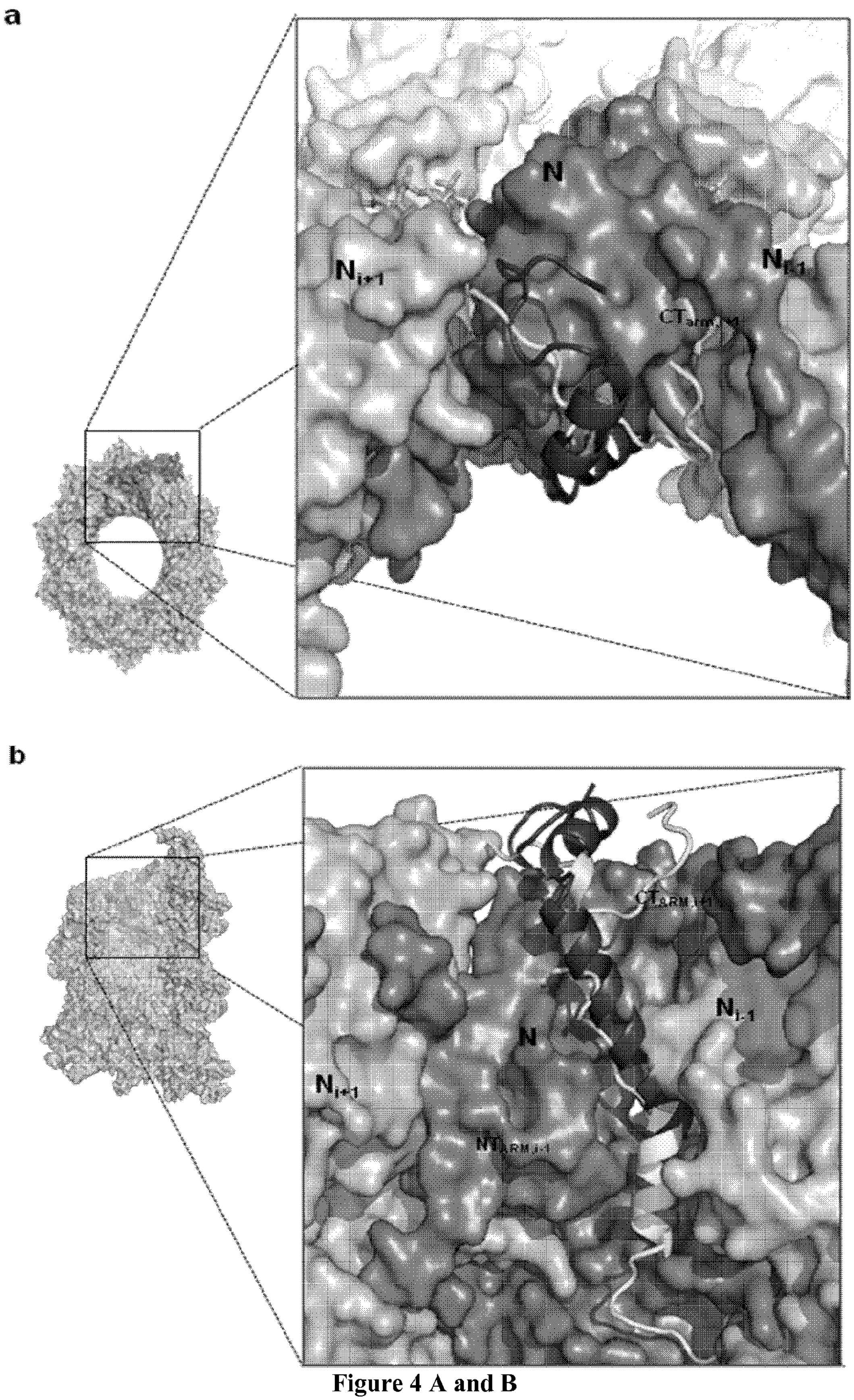
Figure 4 A and B

C
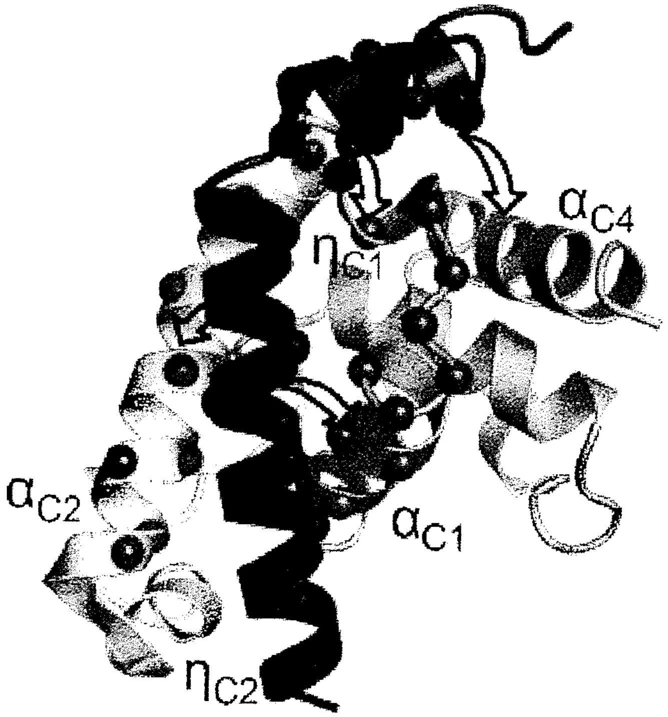
D
d
| | | 260 270 | | |
|---|---|---|---|---|
| NiV | 253 | SDIGNYVEETGMAGFFATIRF | 273 | SEQ ID NO: 41 |
| MeV | 253 | CDIDTYIVEAGLASFTLTIKF | 273 | SEQ ID NO: 42 |
| MuV | 253 | GDIGKYIENSGLTAFFLTLKY | 273 | SEQ ID NO: 43 |
| NDV | 251 | GDVDSYIRNTGLTAFFLTLKY | 271 | SEQ ID NO: 44 |
Figure 4 C and D

PEPTIDES INCLUDING A BINDING DOMAIN OF THE VIRAL PHOSPHOPROTEIN (P) SUBUNIT TO THE VIRAL RNA FREE NUCLEOPROTEIN ($N^0$)

FIELD OF THE INVENTION

The invention related to isolated peptides including a binding domain of the viral phosphoprotein (P) subunit to the viral RNA free nucleoprotein ($N^0$) which has the property to inhibit the replication of viruses from the subfamily Paramyxovirinae (like Henipavirus, Rubulavirus or Morbillivirus). These isolated peptides may be used for the prevention or the treatment of Paramyxovirinae infection.

BACKGROUND OF THE INVENTION

The Paramyxoviridae are a large family of non-segmented negative-strand RNA viruses (NNV) associated with human respiratory illnesses (e.g. respiratory syncytial virus (RSV), human parainfluenza viruses) and with common childhood diseases such as measles and mumps. Owing to phylogenetic relationships, Paramyxoviridae are divided in two subfamilies, the Paramyxovirinae and the Pneumovirinae, and are classified in the order Mononegavirales with the families Rhabdoviridae, Bornaviridae and Filoviridae[10]. Nipah virus (NiV) is emblematic of emerging viruses; spilling over from its natural bat hosts in South East Asia, this virus causes outbreaks of respiratory and encephalic diseases in various mammals including humans'. Its mortality rate that can exceed 70% in humans, its potential for human-to-human transmission and the absence of vaccine or specific antiviral treatment classify NiV among biosafety level-4 (BSL-4) pathogens.

The genomic RNA of NiV, like that of all NNV, is condensed by a homopolymer of nucleoprotein (N), forming long helical nucleocapsids (NCs). These ribonucleoprotein complexes are the biologically active templates used for RNA synthesis by the viral RNA-dependent RNA polymerase[2,3], and thus the replication of these viruses requires the continuous supply of unassembled N molecules to encapsidate the positive-sense and negative-sense progeny RNA molecules[4].

Consistent with the ability of the NNV NCs to protect genomic RNA against nucleases, the N proteins comprise two globular domains, N-terminal ($N_{NTD}$) and C-terminal ($N_{CTD}$) that completely enwrap the RNA molecule[5-8] (FIG. 1*a*). The N homopolymer is stabilized by lateral contacts and by the exchange of N-terminal ($NT_{ARM}$) and C-terminal subdomains ($CT_{ARM}$) between adjacent protomers[5-8]. The N of Paramyxovirinae has an additional long disordered C-terminal tail ($N_{TAIL}$) that extends outside the NC and binds the C-terminal domain of P ($P_{XD}$)[11-13]. The tight packaging of the RNA raises the hypothesis that N must open and close to accommodate RNA inside the binding groove upon the NC assembly process and to transiently release the RNA template upon passage of the RNA polymerase, but until now, there is no evidence of a conversion between open and closed N forms.

In the absence of other viral proteins, N has a strong tendency to polymerize and assemble on cellular RNAs. In Paramyxoviridae, but also in Rhabdoviridae and perhaps in all NNVs, a viral protein acts as a specific chaperone of nascent N and keeps it in an assembly-competent form ($N^0$), by preventing both its polymerization and its interaction with cellular RNAs[9,14]. Paramyxoviridae and Rhabdoviridae P proteins are modular multifunctional proteins, which comprise a long intrinsically disordered N-terminal region (PNTR) and a C-terminal region (PCTR) with a multimerization domain (PMD) connected by a flexible linker to an NC binding domain (PXD)11,15,16 (FIG. 1*a*) and are therefore highly flexible in solution17. In both families, a short N-terminal region of P is sufficient to fulfill both chaperone roles[9,18]. Here inventors study the soluble NiV $N^0$-P core complex to understand the mechanism of NC assembly.

When expressed in human cells, this P $N^0$-binding domain, comprising the first 40 aa of NiV P, is able to inhibit the replication of Nipah virus. Structure-based mutagenesis validates the $N^0$-P complex as the target for the inhibitory activity of the P peptide and for drug development against highly pathogenic members of the subfamily Paramyxovirinae including NiV. Sequence conservation in the binding interface between N and P among various members of the Paramyxovirinae subfamily raises the possibility of developing a broad spectrum drug against several viruses.

SUMMARY OF THE INVENTION

The invention provides an isolated peptide comprising an amino acid sequence of formula (I):

Valine-Xaa1-Xaa2-Glycine-Leucine-Xaa3-Xaa4-Xaa5-Xaa6-Xaa7-Xaa8, wherein:

Xaa1 is glutamine (Q), serine (S) or asparagine (N), lysine (K), or an equivalent polar amino acid;

Xaa2 is glutamic acid (E), aspartic acid (D), asparagine (N), lysine (K), or an equivalent negatively charged (or acid) amino acid;

Xaa3 is glutamic acid (E), aspartic acid (D), lysine (K), glutamine (Q), serine (S) or asparagine (N);

Xaa4 is cysteine (C), isoleucine (I);

Xaa5 is isoleucine (I), leucine (L) or valine (V) or an equivalent apolar aliphatic amino acid;

Xaa6 is glutamine (Q), lysine (K), arginine (R) or aspartic acid (D);

Xaa7 is alanine (A), or phenylalanine (F) or an equivalent apolar amino acid;

Xaa8 is isoleucine (I), leucine (L) or valine (V) or an equivalent apolar aliphatic amino acid.

In preferred embodiments, Xaa5 is isoleucine (I), and Xaa8 is isoleucine (I). In preferred embodiments, Xaa1 is asparagine (N) or glutamine (Q), Xaa2 is aspartic acid (D) or glutamic acid (E), Xaa3 is asparagine (N) or glutamic acid (E), Xaa4 is isoleucine (I) or cysteine (C), Xaa5 is isoleucine (I), Xaa6 is aspartic acid (D) or glutamine (Q), Xaa7 is phenylalanine (F) or alanine (A), and Xaa8 is isoleucine (I).

The invention also provides an isolated peptide comprising the amino acid sequence of formula (II):

Yaa1-Yaa2-Yaa3-Yaa4-Yaa5-Valine-Xaa1-Xaa2-Glycine-Leucine-Xaa3-Xaa4-Xaa5-Xaa6-Xaa7-Xaa8-Yaa6-Yaa7-Yaa8, wherein Xaa1-Xaa2 Xaa3-Xaa4-Xaa5-Xaa6-Xaa7-Xaa8 are defined above Yaa1 is aspartic acid (D), glutamic acid (E), or an equivalent acidic amino acid, Yaa2 is glutamine (Q) or lysine (K), Yaa3 is alanine (A), leucine (L) or tyrosine (Y), Yaa4 is glutamic acid (E), tyrosine (Y) or arginine (R), Yaa5 is asparagine (N), histidine (H) or leucine (L), Yaa6 is glutamine (Q), lysine (K), or arginine (R), Yaa7 is lysine (K), alanine (A) or glutamic acid (E), Yaa8 is asparagines (N), glutamic acid (E) or serine (S).

In preferred embodiments, Yaa1 is aspartic acid (D). In preferred embodiments, Yaa1 is aspartic acid (D), Yaa2 is lysine (K) or glutamine (Q), Yaa3 is leucine (L) or alanine (A), Yaa4 is glutamic acid (E), Yaa5 is leucine (L) or asparagine (N), Yaa6 is glutamine (Q), Yaa7 is lysine (K), and Yaa8 is asparagines (N).

In a preferred embodiment, the isolated peptide comprises or consists of the sequence SEQ ID NO: 3) or the amino acid sequence ranging from the valine residue at position 7 to the isoleucine residue at position 17 in SEQ ID NO:1 P7-17 of SEQ ID NO:1

In some embodiments, the isolated peptide is linked with at least one cell penetrating peptide, Also encompasses are polynucleotides comprising or consisting of a nucleotidic sequence encoding a peptide according to the invention, The invention further relates to methods for preparing or generating the peptides of the invention.

The invention further relates to a pharmaceutical composition comprising a peptide of the invention, together with a pharmaceutically acceptable carrier, and to the use of the peptides or the pharmaceutical composition according to the invention for treating or preventing Paramyxovirinae infection.

DETAILED DESCRIPTION OF THE INVENTION

The inventors have identified sequence from the viral Phophoprotein P subunit in the N-terminal region which interacts with its partner the unassembled RNA-free viral nucleoprotein ($N^0$)(SEQ ID NO.1: MDKLELVNDGLNIID-FIQKNQKEIQKTYGRSSIQQPSIKD, positions 1-40 of viral Nipah Phosphoprotein P sequence deposited in Swiss-Prot database under accession number Q9IK91). This $N^0$ binding domain corresponds to amino acid positions 1-40. This P $N^0$-binding domain, when expressed in cells, is able to inhibit the replication of Nipah virus. The inventors have identified the molecular protein partner of this peptide (the viral unassembled nucleoprotein $N^0$) and solve the crystal structure of the complex. The inventors have obtained evidence that the peptide competes with the native phosphoprotein P for binding to this protein partner. The interface between the phosphoprotein P and the nucleoprotein $N^0$ is conserved among several members of the viral subfamily Paramyxovirinae (including measles and mumps viruses).

The inventors have also generated shorter isolated peptides from this 1-40 Nipah phosphoprotein P subunit with different lengths: between 11 and 37 amino acids (P6-40, P11-40; P1-20; P20-35 and P7-17) which have the ability to inhibit the phosphoprotein P/nucleoprotein $N^0$ interaction and consecutively to inhibit viral replication.

The inventors have further generated isolated peptides from CDV phosphoprotein P subunit, consisting of residues 1 to 40 (SEQ ID NO.2 MAEEQAYHVSKGLECLKAL-RENPPDIEEIQEVSSLRDQTC, positions 1-40 of viral CDV phosphoprotein P sequence (NCBI Reference strain NC_001921.1)) and shorter peptides P1-22, P9-19, which exhibits a similar activity as the 1-40 Nipah virus phosphoprotein P subunit.

The inventors have further generated, based on this conserved sequence of the phosphoprotein P subunit among the members of the viral subfamily Paramyxovirinae, a consensus peptide that includes the conserved (in bold) and the best residues at the other positions (SEQ ID NO.3: DQAEN-VQEGLECIQAIQKN).

The inventors have further generated isolated peptides from Measles virus phosphoprotein P subunit, consisting of residues 1 to 40 (SEQ ID NO.4: MAEEQARHVKNGLE-CIRALKAEPIGSLAIEEAMAAWSEIS, positions 1-40 of viral MeV phosphoprotein P sequence deposited in Swiss-Prot database under accession number (Q76VZ7_MEASE) and shorter peptide P9-19, which exhibits a similar activity as the 1-40 Nipah virus phosphoprotein P subunit.

The inventors have thus found a new targeted therapy for treating viral infection by members of the Paramyxovirinae subfamily with no available targeted therapy. Said invention is particularly advantageous for treating infections by Rubulaviruses, Henipaviruses, Morbilliviruses.

Definitions

Throughout the specification, several terms are employed and are defined in the following paragraphs.

As used herein, the term "Paramyxovirinae" denotes a subfamily of the Paramyxoviridae. Members of this subfamily are enveloped viruses with a non-segmented, negative, single-stranded RNA genome encapsidated by a virally encoded nucleoprotein (N) within a helical nucleocapsid. Transcription and replication of this (N:RNA) template are carried out by a viral RNA-dependent RNA polymerase complex, made of the phosphoprotein (P) and the large protein (L) (reviewed by Lamb & Kolakofsky, 2001). Association of P with the soluble, monomeric form of N ($N^0$) prevents its illegitimate self-assembly onto cellular RNA. "Paramyxovirinae" include major human pathogens such as parainfluenza virus and measles virus (MV), The different "Paramyxovirinae" genera are:

Genus *Aquaparamyxovirus* (type species Atlantic salmon paramyxovirus: others include Pacific salmon paramyxovirus)

Genus *Avulavirus* (type species Newcastle disease virus)

Genus *Ferlavirus* (Fer-de-Lance virus)

Genus *Henipavirus* (type species Hendravirus; others include Nipah virus)

Genus *Morbillivirus* (type species Measles virus; others include Rinderpest virus, Canine distemper virus, phocine distemper virus, Ovine rinderpest)

Genus *Respirovirus* (type species Sendai virus; others include Human parainfluenza viruses 1 and 3, as well some of the viruses of the common cold)

Genus *Rubulavirus* (type species Mumps virus; others include Achimota virus 1 and 2, Human parainfluenza viruses 2 and 4, Simian parainfluenza virus 5, Menangle virus, Tioman virus, Tuhokovirus 1, 2 and 3)

Genus TPMV-like viruses (type species Tupaia paramyxovirus: other species Mossman virus, Nariva virus and Salem virus)

As used herein, the term "amino acid" refers to natural or unnatural amino acids in their D and L stereoisomers for chiral amino acids. It is understood to refer to both amino acids and the corresponding amino acid residues, such as are present, for example, in peptidyl structure. Natural and unnatural amino acids are well known in the art. Common natural amino acids include, without limitation, alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr), and valine (Val). Uncommon and unnatural amino acids include, without limitation, allyl glycine (AllylGly), norleucine, norvaline, biphenylalanine (Bip), citrulline (Cit), 4-guanidinophenylalanine (Phe(Gu)), homoarginine (hArg), homolysine (hLys), 2-naphtylalanine (2-Nal), ornithine (Orn) and pentafluorophenylalanine.

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan and tyrosine are classified as both polar and aromatic amino acids. Amino acids may further be classified as non-charged, or charged (positively or negatively) amino acids. Examples of positively charged amino acids include without limitation lysine, arginine and histidine. Examples of negatively charged amino acids include without limitation glutamic acid and aspartic acid. Additional amino acids that are classified in each of the above groups are known to those of ordinary skill in the art.

"Equivalent amino acid" means an amino acid which may be substituted for another amino acid in the peptide compounds according to the invention without any appreciable loss of function. Equivalent amino acids will be recognized by those of ordinary skill in the art. Substitution of like amino acids is made on the basis of relative similarity of side chain substituents, for example regarding size, charge, hydrophilicity and hydrophobicity as described herein. The phrase "or an equivalent amino acid thereof" when used following a list of individual amino acids means an equivalent of one or more of the individual amino acids included in the list.

The N- and C-termini of the peptides described herein may be protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH═CH-bond. The peptides described herein may also be protected against proteolysis by the technique of stapled peptides as described by Walensky et al. Science. 2004, 305, 1466-70.

In another aspect of the invention, peptides are covalently bound to a polyethylene glycol (PEG) molecule by their C terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly (D, L-lactide-co-glycolide) (PLGA) (as illustrated in US2007/0184015, SoonKap Hahn et al).

The terms "cell penetrating peptide" or "CPP" are used interchangeably and refer to cationic cell penetrating peptides, also called transport peptides, carrier peptides, or peptide transduction domains. The CPP, as shown herein, have the capability of inducing cell penetration of a peptide fused to the CPP within 30%, 40%, 50%, 60%, 70%, 80%, 90%, or 100% of cells of a given cell culture population, including all integers in between, and allow macromolecular translocation within multiple tissues in vivo upon systemic administration. A cell-penetrating peptide may also refer to a peptide which, when brought into contact with a cell under appropriate conditions, passes from the external environment in the intracellular environment, including the cytoplasm, organelles such as mitochondria, or the nucleus of the cell, in conditions significantly greater than passive diffusion. Such penetrating peptides may be those described in Fonseca S. B. et al., Advanced Drug Delivery Reviews, 2009, 61: 953-964, Johansson et al., Methods in Molecular Biology, 2011, Vol. 683, Chapter 17, Bechara and Sagan, (2013) FEBS letters 587, 1693-1702.; Jones and Sayers (2012), Journal of controlled release: official journal of the Controlled Release Society 161, 582-591; Khafagyel and Morishita, (2012) Advanced drug delivery reviews 64, 531-539; Malhi and Murthy, (2012) Expert opinion on drug delivery 9, 909-935, in WO2004/011595 and in WO2003/011898. All that CPP are incorporated by reference.

By "stringent conditions", it is meant conditions of temperature and ionic strength allowing specific hybridization between two complementary nucleic acid fragments and limiting non-specific binding (Sambrook et al. Molecular Cloning, Second Edition (1989), 9.47-9.62). The temperature conditions are generally comprised between (Tm−5° C.) and (Tm−10° C.), Tm being the theoretical fusion temperature, which is defined as the temperature at which 50% of the paired strands separate. For sequences comprising more than 30 bases, Tm is defined by the formula: Tm=81.5+0.41 (% G+C)+16.6 Log (cations concentration)−0.63 (% formamide)−(600/bases number). For sequences comprising less than 30 bases, Tm is defined by the formula: Tm=4 (G+C)+2 (A+T).

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The term "patient" or "subject" refers to a human or non human mammal, preferably a mouse, cat, dog, monkey, horse, cattle (i.e. cow, sheep, goat, buffalo), including male, female, adults and children.

As used herein, the term "treatment" or "therapy" includes curative and/or prophylactic treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder. Prophylactic treatment refers to any of: halting the onset, reducing the risk of development, reducing the incidence, delaying the onset, reducing the development, as well as increasing the time to onset of symptoms of a particular disorder.

Isolated Peptides

The invention relates to novel isolated peptide derived from N terminal phosphoprotein P of Paramyxovirinae virus, which have capacity to inhibit the phosphoprotein P/nucleoprotein $N^0$ interaction of Paramyxovirinae virus; and/or to inhibit the viral replication of Paramyxovirinae.

In one aspect, the invention provides an isolated peptide, comprising an amino acid sequence of formula (I):

Valine-Xaa1-Xaa2-Glycine-Leucine-Xaa3-Xaa4-Xaa5-Xaa6-Xaa7-Xaa8, wherein:

Xaa1 is glutamine (Q), serine (S), asparagine (N), lysine (K) or an equivalent polar amino acid.

Xaa2 is glutamic acid (E), aspartic acid (D), asparagine (N), lysine (K), or an equivalent negatively charged (or acid) amino acid, Xaa3 is glutamic acid (E), aspartic acid (D), lysine (K) or glutamine (Q), serine (S) or asparagine (N).

Xaa4 is cysteine (C), isoleucine (I),

Xaa5 is isoleucine (I), leucine (L) or valine (V) or an equivalent apolar aliphatic amino acid.

Xaa6 is glutamine (Q), lysine (K), arginine (R) or aspartic acid (D).

Xaa7 is alanine (A), or phenylalanine (F) or an equivalent apolar amino acid.

Xaa8 is isoleucine (I), leucine (L) or valine (V) or an equivalent apolar aliphatic amino acid.

In preferred embodiments, Xaa5 is isoleucine (I), and Xaa8 is isoleucine (I). In preferred embodiments, Xaa1 is asparagine (N) or glutamine (Q), Xaa2 is aspartic acid (D) or glutamic acid (E), Xaa3 is asparagine (N) or glutamic acid (E), Xaa4 is isoleucine (I) or cysteine (C), Xaa5 is isoleucine (I), Xaa6 is aspartic acid (D) or glutamine (Q), Xaa7 is phenylalanine (F) or alanine (A), and Xaa8 is isoleucine (I).

In particular embodiment, the invention provide an isolated peptide selected from the group consisting of:

i) an amino acid sequence ranging from the valine residue at position 7 to the isoleucine residue at position 17 in SEQ ID NO:1 P7-17 of SEQ ID N01;

ii) an amino acid sequence ranging from the valine residue at position 9 to the leucine residue at position 19 in SEQ ID NO:2 P9-19 of SEQ ID N02;

iii) an amino acid sequence substantially homologous to the sequence of (i), or (ii) preferably an amino acid a sequence at least 80% identical to the sequence of (i), or (ii).

The invention also provides an isolated peptide comprising the amino acid sequence of formula (II):

Yaa1-Yaa2-Yaa3-Yaa4-Yaa5-Valine-Xaa1-Xaa2-Glycine-Leucine-Xaa3-Xaa4-Xaa5-Xaa6-Xaa7-Xaa8-Yaa6-Yaa7-Yaa8, wherein Xaa1-Xaa2 Xaa3-Xaa4-Xaa5-Xaa6-Xaa7-Xaa8 are as defined above Yaa1 is aspartic acid (D), glutamic acid (E) or an equivalent acidic amino acid, Yaa2 is glutamine (Q) or lysine (K), Yaa3 is alanine (A), leucine (L) or tyrosine (Y), Yaa4 is glutamic acid (E), or tyrosine (Y) or arginine (R), Yaa5 is asparagine (N), histidine (H) or leucine (L), Yaa6 is glutamine (Q), lysine (K) or arginine (R), Yaa7 is lysine (K), alanine (A) or glutamic acid (E), Yaa8 is asparagines (N), glutamic acid (E) or serine (S).

In preferred embodiments, Yaa1 is aspartic acid (D). In preferred embodiments, Yaa1 is aspartic acid (D), Yaa2 is lysine (K) or glutamine (Q), Yaa3 is leucine (L) or alanine (A), Yaa4 is glutamic acid (E), Yaa5 is leucine (L) or asparagine (N), Yaa6 is glutamine (Q), Yaa7 is lysine (K), and Yaa8 is asparagine (N).

In a preferred embodiment, the peptide comprises or consists of the sequence SEQ ID NO: 3 DQAENVQEGLECIQAIQKN) or the amino acid sequence ranging from the valine residue at position 7 to the isoleucine residue at position 17 in SEQ ID NO:1 P7-17 of SEQ ID N01.

Preferably, an isolated peptide according to the invention has the capacity (i) to inhibit the phosphoprotein P/nucleoprotein $N^0$ interaction of Paramyxovirinae virus; and/or (ii) to inhibit the viral replication of Paramyxovirinae.

The skilled in the art can easily determine whether isolated peptide is biologically active. For example, the capacity to inhibit the phosphosprotein P/nucleoprotein $N^0$ interaction can for example be determined by assessing $N^0$-P fragment complex formation leading to the solubilization of N through inhibition of oligomerisation as shown by changes in cellular localisation and absence of punctuate appearance of N as evidenced by immunofluorescence studies (e.g. as described in Example 2 and FIG. 1*d*). The capacity of associating with nucleoprotein $N^0$ can be determined by analyzing co-localization with nucleoprotein $N^0$ in immunofluorescence studies and/or assessing nucleoprotein $N^0$ binding in cell extract, e.g. using the co-sedimentation protocol described in Rodrigues-Ferreira et al. (2009, PLoS One. 4(10):e7239 2009).

The capacity to inhibit viral replication can for example be determined measuring viral growth titers for virus cultivated in the presence of inhibitors and/or by assessing abolition of syncytia formation through experiments (e.g. as described in Example+FIGS. 3*b,c*). The syncytia formation, which is a hallmark of Paramyxoviruses infection, can be determined using the luciferase-based syncytium quantitative assay described in Barbeau B et al. (J Virol. 1998 September; 72(9):7125-36.).

As used herein, a "biologically active" fragment refers to a fragment exhibiting at least one, preferably all, of the biological activities of a peptide of SEQ ID NO: 1, provided the biologically active fragment retains the capacity of inhibiting viral replication. The biologically active fragment may for example be characterized in that it is capable of inhibiting the phophosprotein P/nucleoprotein $N^0$ interaction when assessed through co-localization experiments (see Example 2 and FIG. 1*d*) and/or inhibiting viral replication when assessed through measurement of viral replication titers and/or syncytia formation experiments and/or qPCR quantification of viral genomic RNA or mRNA (see Example and FIGS. 3*b,c*).

In particular embodiment, the invention provide an isolated peptide selected from the group consisting of:

i) the amino acids sequence consisting of MDKLELVNDGLNIIDFIQKNQKEIQKTYGRSSIQQPSIKD (SEQ ID NO: 1);

ii) an amino acid sequence ranging from the leucine residue at position 6 to the aspartic acid residue at position 40 in SEQ ID NO:1 P6-40 of SEQ ID N01;

iii) an amino acid sequence ranging from the leucine residue at position 11 to the aspartic acid residue at position 40 in SEQ ID NO:1 P11-40 of SEQ ID N01;

iv) an amino acid sequence ranging from the methionine residue at position 1 to the asparagine residue at position 20 in SEQ ID NO:1 P1-20 of SEQ ID N01;

v) an amino acid sequence ranging from asparagine residue at position 20 to the glutamine residue at position 35 in SEQ ID NO:1 P20-35 of SEQ ID N01;

vi) the amino acids sequence consisting of MAEEQAY-HVSKGLECLKALRENPPDIEEIQEVSSLRDQTC (SEQ ID NO: 2);

vii) an amino acid sequence ranging from the methionine residue at position 1 to the asparagine residue at position 22 in SEQ ID NO:2 P1-22 of SEQ ID NO2;

viii) the amino acids sequence consisting of DQAEN-VQEGLECIQAIQKN (SEQ ID NO: 3)

ix) the amino acids sequence consisting of MAEEQAR-HVKNGLECIRALKAEPIGSLAIEEAMAAWSEIS (SEQ ID NO: 4) P40 MeV x) an amino acid sequence ranging from the valine residue at position 9 to the leucine residue at position 19 in SEQ ID NO:4 P9-19 of SEQ ID N04.

xi) an amino acid sequence substantially homologous to the sequence of (i) to (x) preferably an amino acid a sequence at least 80% identical to the sequence of (i) to (x).

A peptide "substantially homologous" to a reference peptide may derive from the reference sequence by one or more conservative substitutions. Preferably, these homologous peptides do not include two cysteine residues, so that cyclization is prevented. Two amino acid sequences are "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar, identical or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.). The percentage of identity may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties.

According to the invention a first amino acid sequence having at least 80% of identity with a second amino acid sequence means that the first sequence has 80; 81; 82; 83; 84; 85; 86; 87; 88; 89; 90; 91; 92; 93; 94; 95; 96; 97; 98; or 99% of identity with the second amino acid sequence. Amino acid sequence identity is preferably determined using a suitable sequence alignment algorithm and default parameters, such as BLAST P (Karlin and Altschul, 1990).

In some embodiments, the isolated peptide of the invention comprises at most 100 aminoacid (and at least 9). In some embodiments, the polypeptide of the invention comprises 100; 99; 98; 97; 96; 95; 94; 93; 92; 91; 90; 89; 88; 87; 86; 85; 84; 83; 82; 81; 80; 79; 78; 77; 76; 75; 74; 73; 72; 71; 70; 69; 68; 67; 66; 65; 64; 63; 62; 61; 60; 59; 58; 57; 56; 55; 54; 53; 52; 51; 50; 49; 48; 47; 46; 45; 44; 43; 42; 41; 40; 39; 38; 37; 36; 35; 34; 33; 32; 31; 30; 29; 28; 27; 26; 25; 24; 23; 22; 21; 20; 19; 18; 17; 16; 15; 14; 13; 12; 11; 10 or 9 amino acids. In some embodiments, the polypeptide of the invention comprises less than 50 amino acids. In some embodiments, the polypeptide of the invention comprises less than 30 amino acids. In some embodiments, the polypeptide of the invention comprises less than 25 amino acids. In some embodiments, the polypeptide of the invention comprises less than 20 amino acids. In some embodiments, the polypeptide of the invention comprises less than 15 amino acids.

Chimeric Peptide

In some embodiments, the isolated phosphoprotein P peptide is linked with at least one cell penetrating peptide (CPP), forming a chimeric peptide.

In a preferred embodiment, the cell penetrating peptide comprises or consists of:

Tat peptide, polyarginines peptide, HA2-R9 peptide, Penetratin peptide, Transportan peptide, Vectocell® peptide, maurocalcine peptide, decalysine peptide, HIV-Tat derived PTD4 peptide, Hepatitis B virus Translocation Motif (PTM) peptide, mPrP1-28 peptide, POD, pVEC, EB1, Rath, CADY, Histatin 5, Antp peptide, Cyt86-101 peptide, DPT peptide.

By "Tat peptide", it is meant a peptide having the sequence RKKRRQRRR (SEQ ID NO: 5 Tat peptide 2) or YGRKKRRQRRR, (SEQ ID NO: 6).

By "polyarginines peptide", it is meant a peptide consisting of at least 9 arginines. Preferably, a polyarginine peptide is a peptide having the sequence R9 (SEQ ID NO: 7) or $R_{11}$ (SEQ ID NO: 8).

By "HA2-$R_9$ peptide", it is meant a peptide having the sequence GLFEAIEGFIENGWEGMIDGWYG-$R_9$ (SEQ ID NO: 9).

By "Penetratin peptide", it is meant a peptide having the sequence RQIKIWFQNRRMKWKK (SEQ ID NO: 10).

By "Transportan peptide", it is meant a peptide having the sequence GWTLNSAGYLLGKINLKALAALAKKIL (SEQ ID NO: 11).

By "Vectocell® peptide", it is meant a peptide originating from human heparin binding proteins and/or anti-DNA antibodies.

By "Maurocalcine peptide", it is meant a peptide having the sequence GDCLPHLKLCKENKDCCSKKCKRRGT-NIEKRCR (SEQ ID NO: 12).

By "decalysine peptide", it is meant a peptide having the sequence KKKKKKKKKK ($K_{10}$) (SEQ ID NO: 13).

By "HIV-Tat derived PTD4 peptide", it is meant a peptide having the sequence YARAAARQARA (SEQ ID NO: 14).

By "Hepatitis B virus Translocation Motif (PTM) peptide", it is meant a peptide having the sequence PLSSIF-SRIGDP (SEQ ID NO: 15).

By "mPrP1-28 peptide", it is meant a peptide having the sequence MANLGYWLLALFVTMWTDVGLCKKRPKP (SEQ ID NO: 16).

By "POD peptide", it is meant a peptide having the sequence GGG$(ARKKAAKA)_4$ (SEQ ID NO: 17).

By "pVEC peptide", it is meant a peptide having the sequence LLIILRRRRIRKQAHAHSK (SEQ ID NO: 18).

By "EB1 peptide", it is meant a peptide having the sequence LIRLWSHLIHIWFQNRRLKWKKK (SEQ ID NO: 19).

By "Rath peptide", it is meant a peptide having the sequence TPWWRLWTKWHHKRRDLPRKPE (SEQ ID NO: 20).

By "CADY peptide", it is meant a peptide having the sequence GLWRALWRLLRSLWRLLWRA (SEQ ID NO: 21).

By "Histatin 5 peptide", it is meant a peptide having the sequence DSHAKRHHGYKRKFHEKHHSHRGY (SEQ ID NO: 22).

By "Antp peptide", it is meant a peptide having the sequence RQIKIWFQNRRMKWKK (SEQ ID NO: 23).

By "Cyt86-101 peptide", it is meant a peptide having the sequence KKKEERADLIAYLKKA (SEQ ID NO: 24).

By "DPT peptide", it is meant a peptide having the sequence VKKKKIKREIKI (SEQ ID NO: 25)

In another preferred embodiment, the phosphoprotein P peptide is linked to two, three or more penetrating peptides.

As isolated peptide the chimeric peptide according to the invention has the capacity to inhibit the phosphoprotein P/nucleoprotein $N^0$ interaction of Paramyxovirinae virus; and/or to inhibit the viral replication of Paramyxovirinae.

Nucleic Acids

The invention also relates to a polynucleotide comprising or consisting of a nucleotidic sequence encoding an isolated peptide according to the invention.

In an embodiment, the polynucleotide comprises or consists of a nucleotidic sequence selected from:

```
P40 Nipah
                                   SEQ ID NO: 26
(5'-ATGGATAAATTGGAACTAGTCAATGATGGCCTCAATATTATTGAC

TTTATTCAGAAGAACCAAAAAGAAATACAGAAGACATACGGACGATCAA

GTATTCAACAACCCAGCATCAAAGAT-3');

P40 CDV
                                   SEQ ID NO: 27
(5'-ATGGCAGAGGAACAGGCCTACCATGTCAGCAAAGGGCTGGAATGC

CTCAAAGCCCTCAGAGAGAATCCTCCTGACATTGAGGAGATTCAAGAGG

TCAGCAGCCTCAGAGACCAAACCTGC-3');

P40 MeV
                                   SEQ ID NO: 28
(5'-ATGGCAGAAGAGCAGGCACGCCATGTCAAAAACGGACTGGAATGC

ATCCGGGCTCTCAAGGCCGAGCCCATCGGCTCACTGGCCATCGAGGAAG

CTATGGCAGCATGGTCAGAAATATCA-3');
```

respectively coding the peptide of sequences SEQ ID NO: 1, 2, 4.

The invention also relates to polynucleotides with nucleotidic sequences complementary to one of the sequence as described above and to sequences hybridizing to said polynucleotides under stringent conditions.

The invention further relates to a genetic construct consisting of or comprising a polynucleotide as defined herein, and regulatory sequences (such as a suitable promoter(s), enhancer(s), terminator(s), etc.) allowing the expression (e.g. transcription and translation) of a peptide according to the invention in a host cell.

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to ii) one or more regulatory elements, such as a promoter and optionally a suitable terminator; and optionally also iii) one or more further elements of genetic constructs known per se; in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promotor). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence as defined herein, e.g. a coding sequence, to which it is operably linked.

Some particularly preferred promoters include, but are not limited to, promoters known per se for the expression in the host cells mentioned herein; and in particular promoters for the expression in the bacterial cells.

A selection marker should be such that it allows, i.e. under appropriate selection conditions, host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism.

An expression marker or reporter gene should be such that—in the host cell or host organism—it allows for detection of the expression of a gene or nucleotide sequence present on the genetic construct. An expression marker may optionally also allow for the localisation of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein. For some (further) non-limiting examples of the promoters, selection markers, leader sequences, expression markers and further elements that may be present/used in the genetic constructs of the invention, such as terminators, transcriptional and/or translational enhancers and/or integration factors, reference is made to the general handbooks such as Sambrook et al. Other examples will be clear to the skilled person.

The genetic constructs of the invention may generally be provided by suitably linking the nucleotide sequence(s) of the invention to the one or more further elements described above, for example using the techniques described in the general handbooks such as Sambrook et al.

Often, the genetic constructs of the invention will be obtained by inserting a nucleotide sequence of the invention in a suitable (expression) vector known per se.

The nucleic acids of the invention and/or the genetic constructs of the invention may be used to transform a host cell or host organism, i.e. for expression and/or production of the peptides of the invention.

Thus, in another aspect, the invention relates to a host or host cell that expresses (or that under suitable circumstances is capable of expressing) a peptide of the invention; and/or that contains a polynucleotide of the invention or genetic construct of the invention. Suitable hosts or host cells will be clear to the skilled person, and may for example be any suitable fungal, prokaryotic or eukaryotic cell or cell line or any suitable fungal, prokaryotic or eukaryotic organism, for example: a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis*; a fungal cell, including but not limited to cells from species of *Trichoderma*, for example from *Trichoderma reesei*; of *Neurospora*, for example from *Neurospora crassa*; of *Sordaria*, for example from *Sordaria* macrospore; of *Aspergillus*, for example from *Aspergillus niger* or from *Aspergillus sojae*; or from other filamentous fungi; a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica*; an amphibian cell or cell line, such as *Xenopus* oocytes; an insect-derived cell or cell line, such as cells/cell lines derived from lepidoptera, including but not limited to *Spodoptera* SF9 and Sf21 cells or cells/cell lines derived from *Drosophila*, such as Schneider and Kc cells; a plant or plant cell, for example in tobacco plants; and/or a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells.

Method of Preparing Peptides

The invention further relates to methods for preparing or generating the peptides of the invention.

The peptides of the invention may be produced by any well-known procedure in the art, including chemical synthesis technologies and recombinant technologies.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoe (t-butoxycarbonyl), Cl-Z (2-chlorobenzyloxycarbonyl), Br-Z (2-bromobenzyloyycarbonyl), Bzl (benzyl), Fmoc (9-fluorenylmcthoxycarbonyl), Mbh (4, 4'-dimethoxydibenzhydryl), Mtr (4-methoxy-2, 3, 6-trimethylbenzenesulphonyl), Trt (trityl), Tos (tosyl), Z (benzyloxycarbonyl) and Clz-Bzl (2, 6-dichlorobenzyl) for the amino groups; NO2 (nitro) and Pmc (2,2, 5,7, 8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

Alternatively, the peptide may be synthesized using recombinant techniques. In this case, a nucleic acid and/or a genetic construct according to the invention as described above is/are used.

The method of producing the peptide may optionally comprise the steps of purifying said peptide, chemically modifying said peptide, and/or formulating said peptide into a pharmaceutical composition.

Pharmaceutical Compositions

The invention further relates to a pharmaceutical composition comprising a peptide of the invention, together with a pharmaceutically acceptable carrier.

More particularly, the invention relates to a pharmaceutical composition comprising an isolated peptide of the invention or a chimeric peptide of the invention, together with a pharmaceutically acceptable carrier.

The peptide is formulated in association with a pharmaceutically acceptable carrier.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The dosing is selected by the skilled person so that a anti-infectious effect is achieved, and depends on the route of administration and the dosage form that is used. Total daily dose of a peptide administered to a subject in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Therapeutic Applications

The isolated peptide and the chimeric peptide as defined above, the pharmaceutical composition of the invention may be used for treating Paramyxovirinae infection.

The invention thus also relates to a peptide, or a chimeric peptide of the invention for use for treating Paramyxovirinae infection.

In particular, the isolated peptide, or a chimeric peptide of the invention may have the ability to decrease the virus load in a subject of at least 50%, 60%, 70%, 80%, 90% or 100%.

The invention also provides a method of treatment of a Paramyxovirinae infection in a patient in need thereof, which method comprises administering said patient with an isolated peptide, or a chimeric peptide of the invention.

The Parmyxovirinae infection is due to a virus that belongs to the genus selected between *Rubulavirus* infection, Avulavivirus infection, *Henipavirus* infection, *Henipavirus*-like infection, *Morbillivirus* infection, *Morbillivirus*-like (TPMV-like viruses) infection or *Ferlavirus* infection The *Henipavirus* infection is in particular but not limited to an infection with the *Nipah* virus (NiV) or with the Hendra virus (HeV).

The *Morbillivirus* infection is in particular but not limited to, an infection with the Measles virus (MeV) or Rinderpest virus.

The *Rubulavirus* infection is in particular but not limited to, an infection with the Mumps virus and parainfluenza type 2, 4 viruses.

The invention will be further illustrated by the following figures and examples. However, these examples and figures should not be interpreted in any way as limiting the scope of the present invention.

FIGURES

FIG. 1: Structure of reconstituted NiV $N^0$-P complex in solution and in crystal. (a) Schematic architecture of NiV N and P proteins. $N_{NTD}$, N-terminal domain of N core; $N_{CTD}$, C-terminal domain of N core; $NT_{ARM}$, N-terminal arm of N; $CT_{ARM}$, C-terminal arm of N; $P_{NTR}$, N-terminal region of P; $P_{CTR}$, C-terminal region of P; $P_{MD}$, multimerization domain of P; $P_{XD}$, C-terminal X domain of P. Boxes and lines show structured domains and intrinsically disordered regions, respectively. Arrows show the recombinant constructs used in this work. (b) Size exclusion chromatography (SEC) combined with on-line detection by multi-angle laser light scattering (MALLS) and refractometry (RI). The inset shows a Coomassie blue stained SDS-PAGE. The theoretical molecular mass calculated for a heterodimeric complex is 45,613 Da. (c) Difference intensity profile of $^1H$-$^{15}N$ HSQC spectra of $^{15}N$-labeled $P_{100}$ in isolation and in complex with $N^0$. (d) Fluorescence images of 293T transfected cells expressing NiV N, P40-wt peptide in fusion with GFP, or both proteins (bottom panels). Images are representative of one of three independent experiments. Scale bars (left panels) represent 10 μm. (e) View of the crystal structure of NiV $N_{32-383}{}^0$-$P_{50}$ complex with cartoon representation. $N_{32-383}$ is shown together with P50. The location of some secondary structure elements and of the N-terminal arm and C-terminal arm and tail are indicated. The C- and N-terminal residues of the P fragment are indicated.

FIG. 2: Comparison of NiV and RSV N proteins reveals an open-to-closed conformational change. (a) View of the structures of NiV N and RSV N (PDB code 2WJ8; ref 5) aligned in similar orientations. (b) Structural comparisons of NiV $N_{32-383}$ in its crystal structure (left panel) and in a hypothetical closed conformation (right panel) with RSV N taken from the NC-like complex (PDB code 2WJ8; ref 5). NiV $N_{32-383}$, RSV N and the RNA bound to RSV N are shown. The lines in the left panel show the direction of $\alpha_{N9}$ axis in each protein. The hypothetical closed form of NiV N was obtained by independently aligning NiV $N_{NTD}$ and $N_{CTD}$ on the corresponding domains of RSV N. (c) Front view of the RNA binding site in RSV N with a cartoon representation. Residues interacting with RNA and conserved in several members of the Paramyxovirinae (K170, R184, R185, R338 and Y337) are shown in stick representation. (d) Front view of the putative RNA binding groove of NiV N in its open and hypothetical closed conformations. The residues corresponding to those shown in FIG. 2*c* are shown with stick representation (K178, R192, R193, R352 and Y354). (e) Side view of the RNA binding site in RSV N with a cartoon representation. Two glycine residues (G241 and G245) forming a flat surface on helix $\alpha_{N9}$ and interacting with base 1 of the six-nucleotide bound to each N protomer are shown in yellow. (f) Multiple sequence alignment among several members of the subfamily Paramyxovirinae: MeV, measles virus (*Morbillivirus*); MuV, mumps virus (*Rubulavirus*); NDV, Newcastle disease virus (*Avulavirus*). (g) Side view of the putative RNA binding groove of NiV N in its open and hypothetical closed conformations. The RNA molecule (shown) is docked against NiV $N_{CTD}$ as in RSV NC.

FIG. 3: Conservation of the $N^0$-P interface and inhibition of NiV replication by a $N^0$-binding peptide of P. (a) View of the NiV $N_{32\text{-}383}{}^0$-$P_{50}$ complex with surface and conservation representations for $N_{32\text{-}383}$ and with cartoon and stick representations for $P_{50}$. The conservation in N derived from multiple sequence alignment is displayed on the surface of NiV N. The sidechains of conserved residues in P N-terminal region are shown in stick representation. (b) Quantification of the effect of peptide expression on viral replication. Viral titer measured 48 h after infection with NiV (MOI 0.01) in culture supernatant of 293T cells transfected with varying amounts (2 μg to 0.125 μg; bars 1 to 5) of plasmids coding for GFP alone (Control), $P_{40\text{-}wt}$, $P_{40\text{-}G10R}$ or $P_{40\text{-}117R}$. Shown are means from three independent experiments. Error bars represent s.d. (n=6; ANOVA test: * indicates values for which P<0.05). Ø indicates absence of plasmid. (c) Visual analysis of syncytia formation in NiV-infected cells expressing GFP (Control) or GFP-$P_{40\text{-}wt}$. or -$P_{40\text{-}G10R}$. Arrows show examples of typical syncytia formation. Images are representative of those obtained in one of three independent experiments. Scale bars (left panels) represent 50 μm.

FIG. 4: Chaperone activities of NiV P. (a) Top view of one RSV N protomer within the N-RNA complex, shown with surface representation for $N_{CORE}$ aligned with $N_{CTD}$ of NiV $N_{32\text{-}383}{}^0$-$P_{50}$ complex (PDB codes 2WJ8 and 4BKK; ref 5). The $NT_{ARM}$ of the $N_{i-1}$ RSV N protomer and the $CT_{ARM}$ of the $N_{i+1}$ RSV N protomer are shown with cartoon representation. Only $P_{50}$ of the NiV complex is shown with cartoon representation. The inset shows the localization of RSV N protomer within the NC. (b) Front view of the same structural overlay. The inset shows the localization of RSV N protomer within the NC. (c) View of NiV $P_{50}$ bound to $N_{CTD}$ in the $N_{32\text{-}383}{}^0$-$P_{50}$ complex with cartoon representation. The latch in $N_{CTD}$ is shown. The $C_\alpha$ of residues making contacts between $P_{50}$ and $N_{CTD}$ are shown for $P_{50}$ or $N_{32\text{-}383}{}^0$ as spheres. Arrows indicate the connections between P50 and the helices $\alpha_{C1}$, $\eta_{C1}$, $\alpha_{C2}$ and $\alpha_{C4}$ of $N_{CTD}$. (d) Multiple sequence alignment among several members of the subfamily Paramyxovirinae. (e) Structural overlay of RSV N-RNA complex and NiV $N_{32\text{-}383}$ with cartoon representation. Residues Y258 and G305 of NiV N and residues Y251 and G295 of RSV N are shown with stick representation. The arrow indicates the hypothetical rotation of Y258 upon P release.

FIG. 5: Inhibition of NiV or CDV replication by a $N^0$-binding peptide of P. A. Peptides derived from the $N^0$-binding region of P ($P_{40}$) from NiV inhibit viral growth of both NiV and CDV. 293T cells were transfected with 1 μg of plasmid encoding either w.t. $P_{40}$-CDV in fusion with GFP (P40-CDV), w.t. $P_{40}$-NiV either in fusion with GFP ($P_{40}$-NIV) or separately (pCG $P_{40}$-NIV), GFP alone (MOCK) or no plasmid (NT). 24 h later cells were infected with either NiV (black bars) or CDV (white bars) (MOI 0.01). Virus titers in culture supernatants were measured 48 h after infection. B. Inhibition of CDV replication by both NiV- and CDV-derived peptides is dose-dependant. Cells were transfected as above with decreasing amounts of "P" plasmids ranging from 1 μg to 0.5 μg as indicated, or 1 μg of either GFP-encoding plasmid (MOCK) or empty plasmid (NT). 24 h post-transfection cells were infected with CDV (MOI 0.01). Virus titers in culture supernatants were measured 72 h after infection.

EXAMPLES

Example 1

Material & Methods

Reconstitution of the $N^0$-P core complex. Constructs comprising residues 1-50 (P50) of P and residues 32-383 ($N_{32\text{-}383}$) or 32-402 of N ($N_{32\text{-}402}$) from the Malaysian isolate UMMC1 of *Nipah* virus (Uniprot numbers Q9IK91 and Q9IK92) were cloned in pETM40 vector in fusion with an N-terminal maltose binding protein (MBP) tag. All proteins were expressed in *E. coli* BL21 (DE3) Rosetta cells. Cells were grown at 37° C. in LB medium until O.D. reached 0.6, and protein expression was induced overnight at 20° C. by addition of isopropyl-β-D-thiogalactoside (IPTG) to a final concentration of 1 mM. Cells were harvested and the pellet was suspended in buffer A for P construct (20 mM Tris-HCl buffer at pH 7.5 containing 150 mM NaCl, 50 mM arginine, 50 mM glutamate and 0.5 mM tris(2-carboxyethyl)phosphine (TCEP)) and in buffer B for N constructs (Tris-HCl buffer at pH 7.5 containing 150 mM NaCl). All buffers were supplemented with Complete protease inhibitor cocktail (Roche). Cells were disrupted by sonication, and the crude extract was cleared by centrifugation at 45,000 g at 4° C. for 20 min. The supernatant was loaded onto an amylose resin column (New England Biolabs) equilibrated in buffer A or B. The column was washed with 10 volumes of buffer A or B containing 500 mM NaCl and the protein was eluted with 50 mM maltose (Sigma) in buffer A or B.

The P-MBP fusion protein was cleaved with TEV protease to remove the MBP tag. The protease was added at an approximate weight ratio of 100:1 (fusion protein:TEV) and digest was performed in buffer A overnight at 4° C. After concentration using Vivaspin concentrators (GE Healthcare) with a 3 kDa cut-off, the protein solution was loaded onto a S75 Superdex (GE Healthcare) column equilibrated in buffer A at 4° C. The purified P peptide was mixed with purified N-MBP, and the mixture was incubated overnight at 4° C. After concentration, the solution was loaded onto a S75 Superdex column equilibrated in buffer A. The fractions containing the $N^0$-MBP-P complex were pooled, and the MBP tag was cleaved by incubation overnight at 4° C. in the presence of TEV protease at a weight ratio of 100:1. The solution was concentrated and loaded onto a S75 Superdex (GE Healthcare) column coupled to a short amylose resin (NEB) column equilibrated in buffer B to completely remove cleaved MBP. The fractions containing the $N^0$-P complex were pooled and concentrated using Amicon concentrators (Millipore) with a 10 kDa cut-off. During the purification process, protein purity was checked by SDS-PAGE.

A construct comprising residues 1-100 ($P_{100}$) of P was cloned in pET28 vector with a C-terminal His-tag and expressed in *E. coli* BL21 (DE3) Rosetta cells. To produce unlabeled $P_{100}$, cells were grown at 37° C. in LB medium until O.D. reached 0.6, and protein expression was induced overnight at 20° C. by addition of isopropyl-β-D-thiogalactoside (IPTG) to a final concentration of 1 mM. For the $^{13}C$-$^{15}N$ labeled $P_{100}$, cells were grown in M9 minimal medium supplemented with MEM vitamins (Gibco), with 1.0 $g \cdot L^{-1}$ of $^{15}NH_4Cl$ and 4.0 $g \cdot L^{-1}$ of $^{13}C$ glucose as previously described[24]. Cells were harvested and the pellet was suspended in buffer A supplemented with Complete protease inhibitor cocktail (Roche). Cells were disrupted by sonication, and the crude extract was cleared by centrifugation at 45,000 g at 4° C. for 20 min. The supernatant was loaded onto His Select resin (Sigma) column pre-equilibrated in buffer A. The column was washed with 10 volumes of buffer A containing 500 mM NaCl and 10 mM imidazole (Sigma) and the protein was eluted in buffer A containing 300 mM imidazole. The fractions containing the peptide were pooled and concentrated using Vivaspin concentrators (GE Healthcare) with a 5 kDa cut-off. The solution was loaded onto a S200 Superdex column equilibrated in buffer A at 4° C. Fractions containing the peptide were pooled and concentrated. For NMR experiments, the $N_{32-402}{}^{0}$-$P_{100}$ complex was reconstituted as described above, and buffer A was exchanged with 20 mM Bis-Tris buffer at pH 6.0 containing 150 mM NaCl, 50 mM arginine, 50 mM glutamate and 0.5 mM TCEP.

To produce a selenomethionine substituted of $N_{32-383}$, cells were grown at 37° C. in M9 minimal medium supplemented with MEM vitamins (Gibco), with 1.0 $g \cdot L^{-1}$ of $NH_4Cl$ and 2.0 $g \cdot L^{-1}$ of glucose until O.D. reached 0.6. Then, the temperature was lowered to 20° C. and the culture was supplemented with a mix of amino acids containing 100 mg Lys, 100 mg Phe, 100 mg Thr, 50 mg Ile, 50 mg Leu, 50 mg Val and 50 mg SelenoMet per liter of medium and incubated for 45 minutes. Protein expression was induced overnight at 20° C. by addition of isopropyl-β-D-thiogalactoside (IPTG) to a final concentration of 1 mM. The selenomethionine derivative was purified as described above.

SEC-MALLS experiments. Size exclusion chromatography (SEC) combined with on-line detection by multi-angle laser light scattering (MALLS) and refractometry (RI) is a method for measuring the absolute molecular mass of a particle in solution that is independent of its dimensions and shape[25]. SEC was performed with a S200 Superdex column (GE Healthcare) equilibrated with 20 mM Tris-HCl buffer containing 150 mM NaCl. The column was calibrated with globular standard proteins. Separations were performed at 20° C. with a flow rate of 0.5 $mL \cdot min^{-1}$. On-line multiangle laser light scattering (MALLS) detection was performed with a DAWN-HELEOS II detector (Wyatt Technology Corp.) using a laser emitting at 690 nm, and protein concentration was measured on-line by the use of differential refractive index measurements using an Optilab T-rEX detector (Wyatt Technology Corp.) and a refractive index increment, do/dc, of 0.185 $mL \cdot g^{-1}$. Weight-averaged molar masses (Mw) were calculated using the ASTRA software (Wyatt Technology Corp.). For size determination, the column was calibrated with proteins of known Stokes radius ($R_S$)[26].

Small angle X-Ray scattering experiments. Small angle X-ray scattering (SAXS) data were collected at the BioSAXS beamline (BM29) of the ESRF (http://www.esrf.eu/UsersAndScience/Experiments/MX/About_our_beamlines/BM29. The scattering from the buffer alone was measured before and after each sample measurement and was used for background subtraction using the program PRIMUS from the ATSAS package [27]. Scattering data were collected at different concentration ranging from 0.3 $mg \cdot mL^{-1}$ to 0.6 $mg \cdot mL^{-1}$ for $P_{100}$ and from 0.55 $mg \cdot mL^{-1}$ to 2.4 $mg \cdot mL^{-1}$ for $N^0$-P complex. No concentration-dependent inter-particle effect was observed. $R_g$ was estimated at low Q values using the Guinier approximation. Ah initio low-resolution bead models of the $N^0$-P complex were computed from the distance distribution function P(r) (Dmax=10 nm) using the program DAMMIN[28]. 20 low-resolution models, obtained from independent reconstructions, were aligned, averaged and filtered with the program DAMAVER[29]. The crystal structure was docked within the envelop using the program SUPCOMB[29].

NMR spectroscopy. The spectral assignment of $P_{100}$ of NiV P protein was obtained at 25° C. in 20 mM Bis-Tris buffer at pH 6.0 containing 150 mM NaCl, 50 mM arginine, 50 mM glutamate and 0.5 mM TCEP using a set of BEST-type triple resonance experiments[30]. The NMR experiments were acquired at a $^1H$ frequency of 800 MHz. A total of six experiments were acquired: HNCO, intra-residue HN(CA)CO, HN(CO)CA and intra-residue HNCA, HN(COCA)CB and intra-residue HN(CA)CB. All spectra were processed in NMRPipe[31], analyzed in Sparky[32] and automatic assignment of spin systems was done using MARS[33] followed by manual verification. The $^1H$-$^{15}N$ HSQC spectrum of $P_{100}$ was compared to the spectrum of purified $N_{32-383}{}^{0}P_{100}$ complex. The intensity ratio of the resonances in the two spectra was used for mapping the binding site of $N^0$ on $P_{100}$. Chemical shifts depend on the backbone φ and ψ dihedral angles, and in disordered systems, they are highly sensitive to the presence of transient secondary structure, commonly expressed in terms of a secondary structure propensity (SSP)[34,35]. The SSP score for isolated $P_{100}$ revealed the presence of several fluctuating α-helices.

Crystallography. We used different constructs of N and P to reconstitute $N^0$-P analogs, but only the $N_{32-383}{}^{0}$P50 complex crystallized. Initial crystallization conditions for the $N_{32-383}{}^{0}$P50 complex were identified at the High Throughput Crystallization Laboratory of the EMBL Grenoble Outstation (https://htxlab.embl.fr). Plate clusters obtained in 22% PEG 3350, 0.2M KBr were used to grow crystal of selenomethionine derivative of the $N_{32-383}{}^{0}P_{50}$ complex by the microseeding method. A plate cluster of native protein was crushed in 50 μl of stabilization solution (20 mM Tris HCl at pH 8 containing 22% PEG 3350, 0.2 M KBr and 0.2 M NaCl,) using the Seed Bead kit (Hampton Research). The seed stock was serially diluted (5, 25, 100, 1000 times), and the drops were set by mixing 0.5 μl of the resulting seed stock, 1 μl of protein solution and 1 μl of precipitant solution. The crystals used for data collection were obtained with protein concentrations of 10 to 20 $mg \cdot mL^{-1}$ in the presence of 16-18% PEG 3350 and 0.2 M KBr and were frozen with 15% glycerol as cryo-protectant. X-ray diffraction data were collected at the ID29 beamline of the ESRF at a wavelength of 0.9793 Å and at a temperature of 100 K and were processed with the XDS package[36]. Initial phases were obtained using the anomalous scattering from selenium atoms by the SAD method with the program HKL2MAP[37]. A model was initially constructed with the Autobuild program[38] from the phenix suite[39] and subsequently refined with the phenix.refine program[40] and Coot[41]. The geometry of the final model was checked with MolProbity[42]. In the model, 97.0% of residues have backbone dihedral angles in the favored region of the Ramachandran plot, 2.77% fall in the allowed regions and 0.23% are outliers. Part of the $\alpha_{N5}$-$\alpha_{N6}$ loop is not visible in the crystal electron density. Figures have been generated with PyMol[43] and Chimera[44]. Low frequency normal modes of $N^0$ were computed with the Elastic Network Model[45]. Multiple sequence alignments were performed with MAFFT[46].

Plasmid construction. Sequences corresponding to residues of NiV P, CDV P or MeV P were cloned in-frame with GFP into the pEGFP-C2 vector (CLONTECH Laboratories) to produce the construct pEGFP-P40 and derivatives (P6-40, P11-40; P1-20; P12-35 and P7-17 of NiV P and P1-22, P9-19 of CDV P and P9-19 of MeV P). NiV P variants P40-G10R and P40-I17R were obtained by site-directed mutagenesis using the QuickChange XL kit (Stratagene). The consensus peptide was produced by PCR cloning into the same pEGFP-C2 vector.

Intracellular localization of N and $P_{40}$. *HEK* 293T cells were obtained from ATCC (HEK 293T/17-ATCC CRL-11268). Cell lines were routinely assayed for *mycoplasma* contamination. 293T cells were cultured in Dulbecco's modified Eagle's medium (DMEM, PAA laboratories) supplemented with 10% fetal calf serum (FCS) (PerbioHyclone). For transfection, cells were grown for 24 h to a confluence of ~50% and were transfected with 0.5 μg of plasmid encoding N, GFP-$P_{40\text{-}wt}$ or both (or empty plasmid as control) using Turbofect transfection reagent (Thermoscientific) at 4:1 ratios of reagent:DNA as recommended. After 48 hours, cells were fixed in 3.7% paraformaldehyde (PFA) in phosphate-buffered saline (PBS) for 45 min, then treated for 30 min with 50 mmol·$L^{-1}$ $NH_4Cl$, and finally, for another 40 min in 0.1% Triton X100-PBS. Immunofluorescence of N was performed with an in-house henipavirus specific rabbit anti-N antibody (at a 1/1000 dilution, antibody specificity was determined by immunofluorescence as shown and by Western blot and Alexa Fluor 555 secondary antibody (Life Technologies) at a 1/1000 dilution. 4,6-diamindino-2-phenylindole (DAPI) diluted in PBS containing 1% bovine serum albumin (BSA) was used for nuclear staining. After several washing steps, pictures were taken using a Zeiss 200M fluorescent microscope. Images were analyzed by Axiovision Software (Zeiss) and ImageJ software[47].

Inhibition of viral replication. All experiments with the *Nipah* virus were performed at INSERM "Laboratoire Jean Mérieux" (Lyon, France) in a biosafety level 4 (BSL-4) containment laboratory. HEK 293T cells were grown as described above for 24 h to a confluence of ~40%. Initially, the cells were transfected with plasmids encoding w.t. $P_{40}$ in fusion with GFP, variants of $P_{40}$ ($P_{40\text{-}G10R}$ or $P_{40\text{-}I17R}$ in fusion with GFP or pEGFP alone as a control using Turbofect reagent as described above. In each case, the amount of plasmid was varied from 2 μg to 0.125 μg. 24 h after transfection, cells were infected with NiV (Malaysian isolate UMMC1) at a multiplicity of infection (MOI) of 0.01. 1 h post-infection (p.i.) virus inoculum was removed and replaced with DMEM media containing 3% FCS. Culture supernatants and cell lysates were collected at 48 h p.i. for TCID50 titration and virus growth was assessed visually by inspecting for syncytial formation. Images of GFP fluorescence were taken using a Zeiss 200M fluorescent microscope. Images were analyzed by Axiovision Software (Zeiss). For Kärber TCID50 determination, serial ten-fold dilutions of viral culture supernatants were used to infect Vero E6 cells in the same way as described above and read 48 h p.i. Significant differences were calculated using an ANOVA test where applicable, n=6.

Example 2

Results

Reconstitution of a Functional NiV $N^0$-P Core Complex

The inventors reconstituted several structural variants of NiV $N^0$-P complex using peptides encompassing the $N^0$-binding region of P and recombinant N molecules, truncated at the $NT_{ARM}$ and the $CT_{ARM}$ and $N_{TAIL}$. By size exclusion chromatography (SEC) combined with multi-angle laser light scattering (MALLS) (FIG. 1*b*) and by small-angle X-ray scattering (SAXS), we found that these reconstituted $N^0$-P core complexes are compact heterodimers with an overall bean-shape typical of other NNV N proteins[18].

The inventors mapped the region of P that directly interacts with $N^0$ by nuclear magnetic resonance (NMR) spectroscopy. To this purpose, we expressed and purified a peptide of 100 amino acids corresponding to the N-terminal region of P ($P_{100}$) and characterized its structural properties. By SEC-MALLS, we showed that the peptide is monomeric in solution and that both its hydrodynamic radius measured by SEC and its radius of gyration measured by SAXS were larger than expected for a globular protein of this molecular mass. In addition, the poor chemical shift dispersion of amide resonances in the heteronuclear single quantum coherence (HSQC) NMR spectrum was typical of disordered protein, but after assigning the NMR spectrum, the secondary structure propensity (SSP) parameter calculated from Cα and Cβ secondary chemical shifts, indicated the presence of five fluctuating α-helices. We then analyzed the HSQC spectrum of P100 bound to $N_{32\text{-}383}$. In a complex of this size (~50 kDa), NMR signals are strongly broadened in protonated samples, precluding their detection, but in the HSQC spectrum we observed resonances corresponding to residues 50 to 100, indicating that this region remains flexible in the complex and that the $N^0$-binding region is comprised within the first fifty N-terminal amino acids of P (FIG. 1*c*).

Accordingly, The inventors demonstrated that a peptide corresponding to the first forty residues of P ($P_{40}$) is sufficient to maintain N in a soluble form in vitro (FIG. 1*d*). In human cells expressing NiV N alone, we observed a punctuate distribution that can be attributed to the inherent self-assembly properties of the protein. In cells co-expressing both N and GFP-fused $P_{40}$ ($P_{40}$-GFP) in a 1:1 ratio, we observed a notably homogenous distribution of N in the cell and the colocalization of N with $P_{40}$, suggesting that the $N^0$-$P_{40}$ complex forms in the intracellular environment and leads to the solubilization of N (FIG. 1*d*).

Crystal structure of NiV $N^0$-P core complex

The NiV $N_{32\text{-}383}{}^0$-$P_{50}$ complex crystallized in space group $P2_12_12_1$ with three heterodimers in the asymmetric unit. We determined the structure at 2.5 Å resolution by the SAD method (FIG. 1*e*). NiV N exhibited the two-domain structure characteristic of NNV N[5-8], defining a basic groove that can bind RNA. Despite the overall low sequence conservation, the N core could be divided into four different parts, $N_{NTD1}$, $N_{NTD2}$ $N_{NTD3}$ and $N_{CTD}$, of which three appear to have a conserved fold among different NNV families (FIG. 2*a*)[5-7,19]. On the basis of their localization in the structure, we defined ten motifs conserved among most members of the Paramyxovirinae and assigned them structural or functional roles.

The N-terminal chaperone region of P is stabilized upon binding to its $N^0$ partner, but only the first 35 residues of P, corresponding to the first fluctuating helix observed in solution (helix $\alpha_{P1}$), were visible in the crystal structure of the $N_{32\text{-}383}{}^0$-$P_{50}$ complex. In the complex, this region formed a 2.9 nm-long helix (helix $\alpha_{P1a}$: aa 1-19) with a 90° kink at residue N20 leading to a short helix (helix $\alpha_{P1b}$: aa 21-28) (FIG. 1*e*. The long helix $\alpha_{P1a}$ docked to a shallow hydrophobic groove of $N_{CTD}$ formed by helices $\alpha_{C1}$, $\eta_{C1}$ and $\alpha_{C2}$ of conserved motif 6 (aa 265-305), and the short helix docks to the top of $N_{CTD}$ (motif 10) (FIG. 1*e*. The complex involves multiple hydrophobic contacts and eight hydrogen bonds for a total surface area buried in the interaction of 1,440 Å$^2$.

NiV N is in an Open Conformation in $N^0$-P Complex

By comparing the structure of NiV $N_{32\text{-}383}{}^0$-$P_{50}$ with that of RSV N in complex with RNA[5], we found that the fold of N is conserved (FIG. 2*a* but that the putative RNA binding groove of NiV $N^0$ is open, with $N_{NTD}$ bowing down by about 30° from $N_{CTD}$ (FIG. 2*b*). We observed that a Tyr residue (Y337) and four out of the five basic residues (K170, R184, R185, R338 and R342) interacting with RNA in RSV N (FIG. 2*c*) are present at equivalent positions (Y354 and K178, R192, R193, R352, respectively) in the helix am, the $\alpha_{N5}$-$\alpha_{N6}$ loop, the helix $\alpha_{N6}$ and the $\alpha_{C3}$-$\alpha_{C4}$ loop of NiV N (FIG. 2D) and are conserved among Paramyxovirinae. However, they are too far apart in NiV $N^0$ to concurrently interact with a RNA molecule. Independent 3D alignments of NiV $N_{NTD}$ and $N_{CTD}$ with RSV N brought these residues into similar positions in both proteins (FIGS. 2*b* and 2*d*), suggesting a common mechanism of conformational switching between open and closed conformations that involves a hinge motion between $N_{CTD}$ and $N_{NTD}$, in agreement with normal mode simulations.

RNA Binding and the Rule of Six

In RSV NCs, each N interacts with seven nucleotides (nt) and base 1 packs on the flat surface of helix $\alpha_{N9}$ formed by two glycine residues (G241 and G245) (FIG. 2*e*)[5]. However, in the Paramyxovirinae sub-family, N binds to only six nt and the genome obeys a rule of six, i.e. a strict requirement for their genome to consist of a multiple of six nt[20,21]. In the putative closed form of NiV N, we found that several residues in helix $\alpha_{N6}$ (conserved motif 3) (FIG. 2*f*) and D254 in helix $\alpha_{N9}$ (conserved motif 5) hinder a similar packing of base 1 (FIG. 2*g*). The presence of motif 3, which is strictly conserved in the Paramyxovirinae sub-family, but is absent in the Pneumovirinae subfamily, might thus explain why the N protein of the Paramyxovirinae binds only six nt and why these viruses obey the rule of six.

Conservation of the $N^0$-P Binding Interface

NNV phosphoproteins vary greatly in length and amino acid sequence[22], with sequence conservation generally becoming undetectable beyond the family level. However, a recent study identified residues in the N-terminal region of P that are conserved among most members of the Paramyxoviridae in spite of an overall distant evolutionary relationship[23]. Most of these conserved residues appeared to be key residues for the interaction with $N^0$ (FIG. 3*a*), whereas mapping residue conservation among Paramyxovirinae onto the surface of NiV N reveals a strong conservation of the binding site for P (FIG. 3*a*). These results thus suggest a conserved structural architecture of the $N^0$-P complex among different genera of the subfamily, and broaden the scope of our NiV $N^0$-P core structure.

Inhibition of NiV Replication

The inventors found that expression of GFP-fused $P_{40}$ peptide in human cells (HEK293T) prior to infection significantly inhibits viral growth in a dose-dependent manner and abolishes syncytia formation, the latter being a hallmark of NiV infection (FIG. 3*b*-*c*). We used the $N_{32\text{-}383}{}^0$-$P_{50}$ crystal structure to design peptide variants that destabilize the interface between $N^0$ and P50, and found that the variants in which conserved residues G10 or 117 are mutated to arginine (G10R, I17R) were less efficient in inhibiting viral replication. These results thus supported the specificity of the interaction observed in the crystal (FIG. 3*b*-*c*). Because the reconstituted $N^0$-P core complex lacks a large part of the P molecule, notably the tetramerization domain and both polymerase and NC binding regions, we hypothesized that $P_{40}$ might inhibit viral growth by trapping $N^0$ in a non-productive complex.

The Chaperone Functions of P

To understand the chaperone functions of $P_{NTR}$, we used RSV N-RNA complex as a model for NiV N-RNA complex (FIG. 4*a*, 4*b*). When we aligned $N_{CTD}$ of NiV $N_{32\text{-}383}{}^0$-$P_{50}$ with the $N_{CTD}$ of one N protomer of the RSV N-RNA complex, we discovered that helix $\alpha_{P1b}$ competes with the $CT_{ARM}$ of the $N_{i+1}$ protomer for the same binding site on N surface (FIG. 4*a*), whereas helix $\alpha_{P1a}$ competes with the $NT_{ARM}$ of the $N_{i-1}$ protomer (FIG. 4*b*). A first role of P is thus to prevent the polymerization of N by interfering with the binding of exchanged subdomains. The structure of NiV $N_{32\text{-}383}{}^0$-$P_{50}$ complex also suggested that bound P prevents NC assembly and RNA binding by trapping $N^0$ in an open conformation without directly interfering with RNA (FIG. 2*g*). The closure of the molecule requires that helices $\alpha_{N5}$ and $\alpha_{N9}$ rotate around pivots near the $N_{NTD}$-$N_{CTD}$ junction (FIG. 2*b*) and thereby that the latch formed by helices $\alpha_{C2}$, $\eta_{C2}$, $\eta_{C3}$, $\eta_{C4}$ move away from the $N_{CTD}$ core. We propose that by bridging helices $\alpha_{C1}$, $\eta_{C1}$, $\alpha_{C2}$ and $\alpha_{C4}$ (FIG. 4*c*), P rigidifies the entire $N_{CTD}$ domain and prevents global conformational changes in N. In addition, the bulky side chain of Y258, a highly conserved residue among Paramyxoviridae (FIG. 4*d*), points inside the RNA binding groove preventing the RNA from coming into close contact with the surface of the protein (FIG. 4*e*). In the RSV N-RNA complex, Y251, similarly located at the end of helix $\alpha_{N9}$, points in the opposite direction and docks against the backbone of a glycine residue in helix $\alpha_{C2}$. A glycine is also conserved at this position in NiV N suggesting that the tyrosine side chain flips away upon RNA binding (FIG. 4*e*), but in the $N^0$-P complex, motion of Y258 is hindered by the presence of the N-terminal end of P. Alternatively, Y258 might interact with one of the RNA bases.

Discussion:

The inventors present the structure of the $N^0$-P core complex of *Nipah* virus, revealing that unassembled $N^0$ is maintained in an open conformation and providing experimental evidence that NNV N switches between open and closed conformations during NC assembly. In the $N^0$-P complex, the N-terminal $N^0$-binding region of P prevents N polymerization by occupying the binding sites for the exchanged subdomains of adjacent N and prevents RNA encapsidation by bridging $N_{CTD}$ and hindering closure of the molecule. We propose a possible scenario for the assembly of $N^0$ molecules along newly synthesized viral RNA by a concerted mechanism of transfer of $N^0$ from the $N^0$-P complex to the nascent RNA molecule, which involves the release of P and the closure of the RNA binding groove. In a first step, we assume that encounter complex forms with the RNA molecule loosely inserted in the open cavity. In a second concerted step, P is released and N grasps the RNA molecule. The release of P from the RNA-bound N liberates the binding site for the NT-arm of the next incoming N molecule. Upon formation of the encounter complex with the next $N^0$-P complex, the $NT_{ARM}$ of the incoming N can bind to the previously bound N. The $CT_{ARM}$ of bound N can bind to the incoming N and help in displacing the P peptide.

In a second or concomitant process, P is released and N closes on the RNA. The $NT_{ARM}$ of the first bound N molecule locks the second N in its closed conformation by bridging $N_{NTD}$ with $N_{CTD}$.

The inventors confirmed that the short $N^0$-binding region of P is sufficient to chaperone $N^0$ and to keep it in a soluble form, but $P_{40}$ inhibited viral replication, indicating that the N-terminal region of P is not sufficient to enable NC assembly and suggesting the involvement of other regions of P in this process. P is a multifunctional, highly flexible molecule, which also possesses binding sites for L or for NCs, and it is thus plausible that interactions with these other viral proteins are necessary to correctly position the $N^0$-P complex at the site of viral RNA synthesis. The attachment of $N^0$-P to the NC, as suggested in FIG. 5*c* would raise the local concentration around the site of RNA synthesis and thereby favor the encapsidation of the viral RNA.

The successful inhibition of NiV infection by the $N^0$-binding peptide of P suggests that the P binding cavity in N can be specifically targeted for designing inhibitors of NiV replication. The structure of the $N^0$-P core complex provides the structural basis for designing small molecules that could prevent the formation of the complex. The strong conservation of the binding interface suggests that NiV $N_{32-383}{}^0$-$P_{50}$ structure is a good structural model for the $N^0$-P complex of other medically-relevant paramyxoviruses and that possibly a broad spectrum drug might be developed against several viruses.

Example 3

Materials and Methods:

Plasmid Construction. Sequences corresponding to residues of NiV P or CDV P (reference strain, Genbank NC_001921.1) were either cloned in-frame with GFP into the pEGFP-C2 vector (CLONTECH Laboratories) to produce the constructs pEGFP-P40-NIV and pEGFP-P40-CDV, or into the vector pCG (ref—Differential transcriptional activation by Oct-1 and Oct-2: interdependent activation domains induce Oct-2 phosphorylation. Tanaka M, Herr W. Cell. 1990 February 9;60(3):375-86. 10.1016/0092-8674 (90)90589-7) containing a GFP-IRES-multicloning site. This vector allows the simultaneous expression of both GFP and p40 peptide separately but from the same bi-cistronic RNA transcript after transfection into mammalian cells.

Inhibition of Viral Replication with NIV and CDV. 293T cells were cultured in Dulbecco's modified Eagle's medium (DMEM, PAA laboratories) supplemented with 10% fetal calf serum (FCS) (PerbioHyclone). All experiments with the *Nipah* virus were performed at INSERM "Laboratoire Jean Mérieux" (Lyon, France) in a biosafety level 4 (BSL4) containment laboratory. All experiments with the canine distemper virus were performed at under biosafety level 2 confinement in a cell culture biosafety cabinet reserved for work with infectious material. Cells were grown as described above for 24 h to a confluence of ~40%. Initially, the cells were transfected with plasmids encoding w.t. $P_{40}$-NIV in fusion with GFP (pEGFP vector) or expressed separately (from the pCG bi-cistronic IRES vector, described above), or w.t. $P_{40}$-CDV in fusion with GFP (pEGFP vector) or either pEGFP/pCG alone as control, using Turbofect following manufacturer's recommendations. 24 h after transfection, cells were infected with either NiV (Malaysian isolate UMMC1) or CDV at a multiplicity of infection (MOI) of 0.01. 1 h post-infection (p.i.) virus inoculum was removed and replaced with DMEM media containing 3% FCS. Culture supernatants and cell lysates were collected at 48 h p.i. for TCID50 titration and virus growth was assessed visually by inspecting for syncytial formation. Pictures of GFP fluorescence were taken using a Zeiss 200M fluorescent microscope. Images were analyzed by Axiovision Software (Zeiss). For Kärber TCID50 determination, serial ten-fold dilutions of viral culture supernatants were used to infect Vero E6 cells in the same way as described above and read 48-72 h p.i.

Results:

Inhibition of NiV or CDV Replication by a $N^0$-Binding Peptide of P.

Figure 5A:
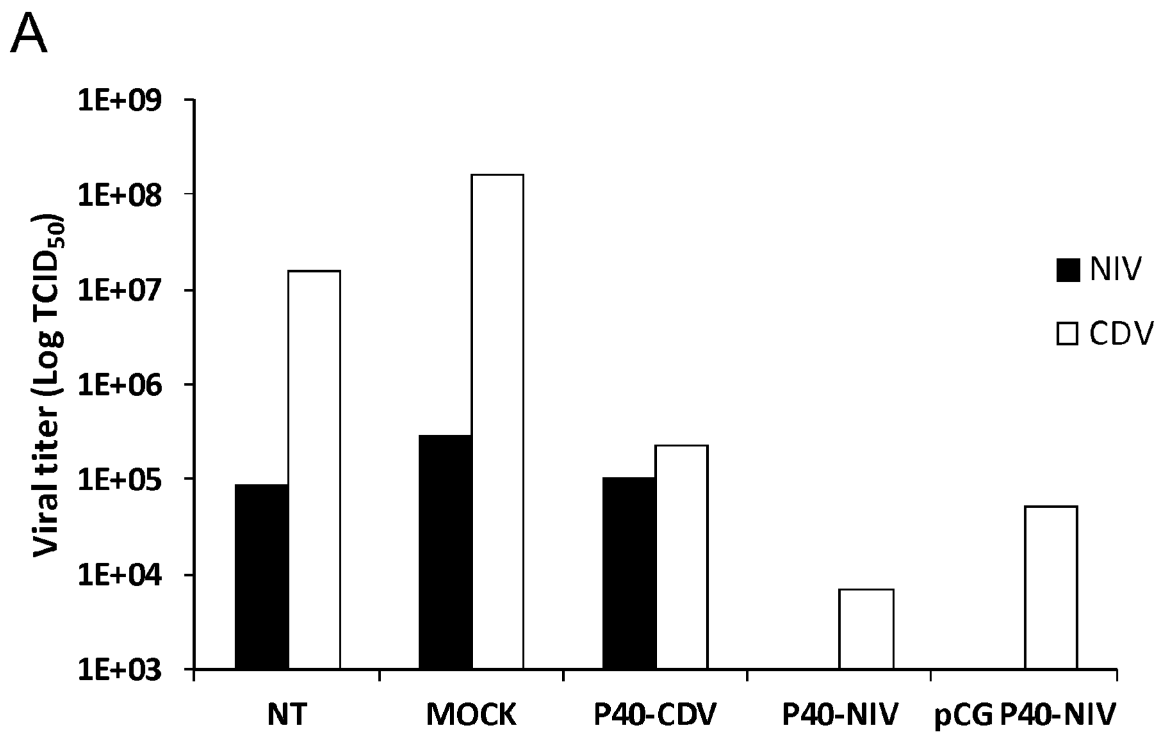
Figure 5B:
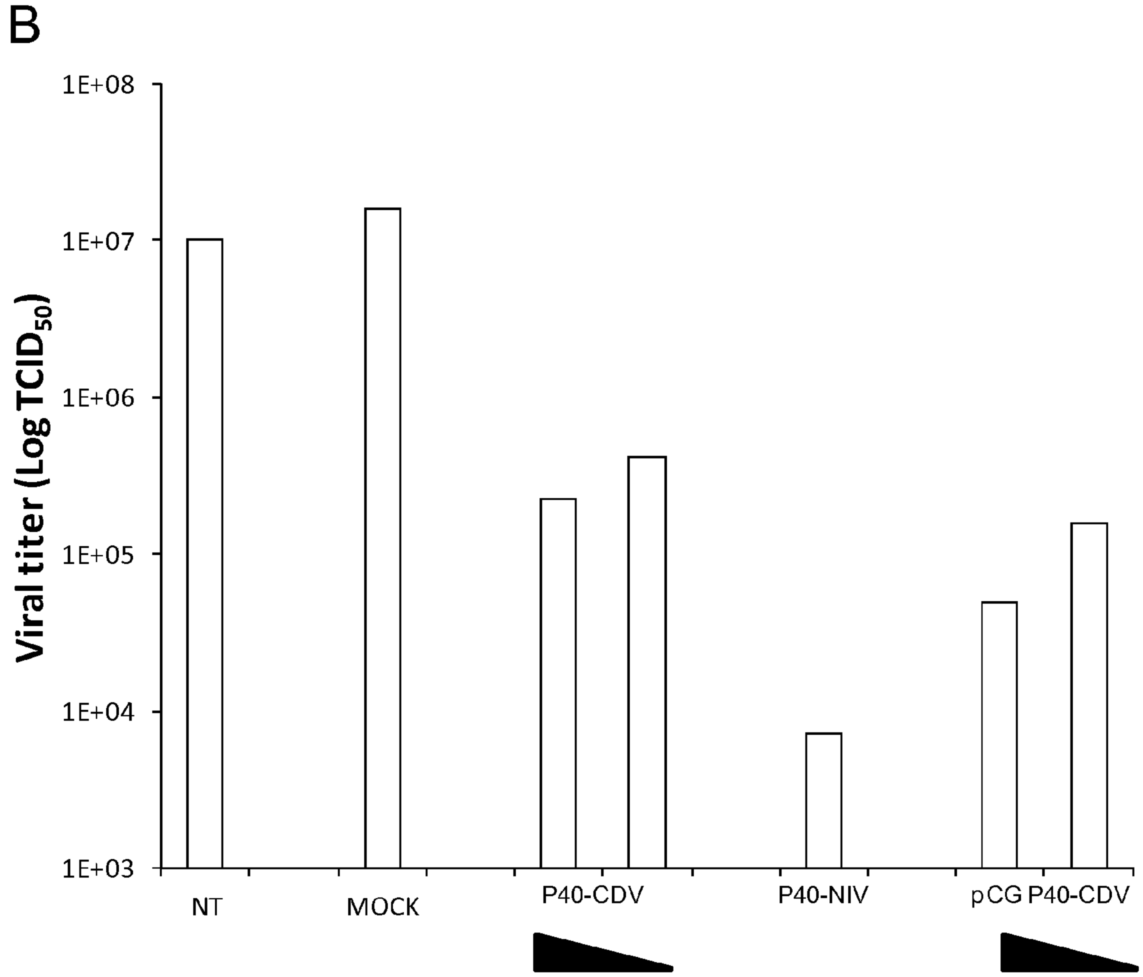

The inventors demonstrated that peptides derived from the $N^0$-binding region of P ($P_{40}$) from NiV inhibit viral growth of both NiV and CDV (FIG. 5A). The inventors also demonstrated that the inhibition of CDV replication by both NiV- and CDV-derived peptides is dose-dependant (FIG. 5B).

REFERENCES

Throughout this application, various references describe the state of the art to which this invention pertains. The disclosures of these references are hereby incorporated by reference into the present disclosure.

1 Chua, K. B. et al. *Nipah* virus: a recently emergent deadly paramyxovirus. Science 288, 1432-1435 (2000).

2 Morin, B., Rahmeh, A. A. & Whelan, S. P. Mechanism of RNA synthesis initiation by the vesicular stomatitis virus polymerase. Embo J. 31, 1320-1329 (2012).

3 Arnheiter, H., Davis, N. L., Wertz, G., Schubert, M. & Lazzarini, R. A. Role of the nucleocapsid protein in regulating vesicular stomatitis virus RNA synthesis. Cell 41, 259-267 (1985).

4 Patton, J. T., Davis, N. L. & Wertz, G. W. N protein alone satisfies the requirement for protein synthesis during RNA replication of vesicular stomatitis virus. J. Virol. 49, 303-309 (1984).

5 Tawar, R. G. et al. Crystal structure of a nucleocapsid-like nucleoprotein-RNA complex of respiratory syncytial virus. Science 326, 1279-1283 (2009).

6 Albertini, A. A. et al. Crystal structure of the rabies virus nucleoprotein-RNA complex. Science 313, 360-363 (2006).

7 Green, T. J., Zhang, X., Wertz, G. W. & Luo, M. Structure of the vesicular stomatitis virus nucleoprotein-RNA complex. Science 313, 357-360 (2006).

8 Desfosses, A., Goret, G., Estrozi, L. F., Ruigrok, R. W. & Gutsche, I. Nucleoprotein-RNA orientation in the measles virus nucleocapsid by three-dimensional electron microscopy. J. Virol. (2010).

9 Curran, J., Marq, J. B. & Kolakofsky, D. An N-terminal domain of the Sendai paramyxovirus P protein acts as a chaperone for the NP protein during the nascent chain assembly step of genome replication. J. Virol. 69, 849-855 (1995).

10 Pringle, C. R. The order Mononegavirales—current status. Arch Virol 142, 2321-2326 (1997).

11 Karlin, D., Ferron, F., Canard, B. & Longhi, S. Structural disorder and modular organization in Paramyxovirinae N and P. J. Gen. Virol. 84, 3239-3252 (2003).

12 Jensen, M. R. et al. Intrinsic disorder in measles virus nucleocapsids. Proc. Natl. Acad. Sci. U.S.A 108, 9839-9844 (2011).

13 Communie, G. et al. Atomic resolution description of the interaction between the nucleoprotein and phosphoprotein of Hendra virus. PLoS Pathog 9, e1003631 (2013).

14 Mavrakis, M. et al. Rabies virus chaperone: identification of the phosphoprotein peptide that keeps nucleoprotein soluble and free from non-specific RNA. Virology 349, 422-429 (2006).

15 Gérard, F. C. A. et al. Modular organization of rabies virus phosphoprotein. J. Mol. Biol. 388, 978-996 (2009).

16 Habchi, J., Mamelli, L., Darbon, H. & Longhi, S. Structural disorder within *Henipavirus* nucleoprotein and phosphoprotein: from predictions to experimental assessment. PLoS One 5, e11684 (2010).

17 Leyrat, C. et al. Ensemble structure of the modular and flexible full-length vesicular stomatitis virus phosphoprotein. J. Mol. Biol. 423, 182-197 (2012).

18 Leyrat, C. et al. Structure of the vesicular stomatitis virus N-P complex. PLoS Pathog 7, e1002248 (2011).

19 Ruigrok, R. W., Crepin, T. & Kolakofsky, D. Nucleoproteins and nucleocapsids of negative-strand RNA viruses. Curr Opin Microbiol 14, 504-510 (2011).

20 Calain, P. & Roux, L. The rule of six, a basic feature for efficient replication of Sendai virus defective interfering RNA. J. Virol. 67, 4822-4830 (1993).

21 Halpin, K., Bankamp, B., Harcourt, B. H., Bellini, W. J. & Rota, P. A. *Nipah* virus conforms to the rule of six in a minigenome replication assay. J. Gen. Virol. 85, 701-707 (2004).

22 Karlin, D. & Belshaw, R. Detecting remote sequence homology in disordered proteins: discovery of conserved motifs in the N-termini of Mononegavirales phosphoproteins. PLoS One 7, e31719 (2012).

23 Marley, J., Lu, M. & Bracken, C. A method for efficient isotopic labeling of recombinant proteins. J. Biomol. NMR 20, 71-75 (2001).

24 Wyatt, P. J. Submicrometer Particle Sizing by Multiangle Light Scattering following Fractionation. J. Colloid Interface Sci. 197, 9-20 (1998).

25 Uversky, V. N. Use of fast protein size-exclusion liquid chromatography to study the unfolding of proteins which denature through the molten globule. Biochemistry 32, 13288-13298 (1993).

26 Konarev, P., Petoukhov, M., Volchkov, V. & Svergun, D. I. ATSAS 2.1, a program package for small-angle scattering data analysis. J. Appl. Cryst. 39, 277-286 (2006).

27 Svergun, D. I. Restoring low resolution structure of biological macromolecules from solution scattering using simulated annealing. Biophys. J. 76, 2879-2886 (1999).

28 Volkov, V. V. & Svergun, D. I. Uniqueness of ab initio shape determination in small-angle scattering. J. Appl. Cryst. 36, 860-864 (2003).

29 Lescop, E., Schanda, P. & Brutscher, B. A set of BEST triple-resonance experiments for time-optimized protein resonance assignment. J. Magn. Reson. 187, 163-169 (2007).

30 Delaglio, F. et al. NMRPipe: a multidimensional spectral processing system based on UNIX pipes. J. Biomol. NMR 6, 277-293 (1995).

31 SPARKY 3 (University of California, San Francisco, 2003).

32 Jung, Y. S. & Zweckstetter, M. Mars—robust automatic backbone assignment of proteins. J. Biomol. NMR 30, 11-23 (2004).

33 Marsh, J. A., Singh, V. K., Jia, Z. & Forman-Kay, J. D. Sensitivity of secondary structure propensities to sequence differences between alpha- and gamma-synuclein: implications for fibrillation. Protein Sci 15, 2795-2804 (2006).

34 Jensen, M. R., Salmon, L., Nodet, G. & Blackledge, M. Defining conformational ensembles of intrinsically disordered and partially folded proteins directly from chemical shifts. J. Am. Chem. Soc. 132, 1270-1272 (2010).

35 Kabsch, W. Xds. Acta Crystallogr D Biol Crystallogr 66, 125-132 (2010).

36 Pape, T. & Schneider, T. R. HKL2MAP: a graphical user interface for phasing with SHELX programs J. Appl. Cryst. 37, 843-844 (2004).

37 Terwilliger, T. C. et al. Iterative model building, structure refinement and density modification with the PHENIX AutoBuild wizard. Acta Crystallogr D Biol Crystallogr 64, 61-69 (2008).

38 Adams, P. D. et al. PHENIX: a comprehensive Python-based system for macromolecular structure solution. Acta Crystallogr D Biol Crystallogr 66, 213-221 (2010).

39 Afonine, P. V. et al. Towards automated crystallographic structure refinement with phenix.refine. Acta Crystallogr D Biol Crystallogr 68, 352-367 (2012).

40 Emsley, P. & Cowtan, K. Coot: model-building tools for molecular graphics. Acta Crystallogr D Biol Crystallogr 60, 2126-2132 (2004).

41 Chen, V. B. et al. MolProbity: all-atom structure validation for macromolecular crystallography. Acta Crystallogr D Biol Crystallogr 66, 12-21 (2010).

42 The PyMOL Molecular Graphics System (DeLano Scientific, Palo Alto, Calif., USA, 2002).

43 Pettersen, E. F. et al. UCSF Chimera—a visualization system for exploratory research and analysis. J Comput Chem. 25, 1605-1612 (2004).

44 Laskowski, R. A. & Swindells, M. B. LigPlot+: multiple ligand-protein interaction diagrams for drug discovery. J. Chem. Inf. Model. 51, 2778-2786 (2011).

45 Suhre, K. & Sanejouand, Y. H. ENemo: a normal mode web server for protein movement analysis and the generation of templates for molecular replacement. Nucleic Acids Res 32, W610-614 (2004).

46 Katoh, K. & Standley, D. M. MAFFT multiple sequence alignment software version 7: improvements in performance and usability. Mol Biol Evol 30, 772-780 (2013).

47 Gouet, P., Robert, X. & Courcelle, E. ESPript/ENDscript: Extracting and rendering sequence and 3D information from atomic structures of proteins. Nucleic Acids Res 31, 3320-3323 (2003).

48 Abramoff, M. D., Magalhaes, P. J. & Ram, S. J. Image Processing with ImageJ. Biophoton. Int. 11, 36-42 (2004).

The invention claimed is:

1. An isolated peptide of at most 100 amino acids comprising an amino acid sequence of formula (I):

Valine-Xaa1-Xaa2-Glycine-Leucine-Xaa3-Xaa4-Xaa5-Xaa6-Xaa7-Xaa8, wherein

Xaa1 is glutamine (Q), serine (S), asparagine (N), lysine (K) or an equivalent polar amino acid;

Xaa2 is glutamic acid (E), aspartic acid (D) asparagine (N), lysine (K), or an equivalent negatively charged, or acid, amino acid;

Xaa3 is glutamic acid (E), aspartic acid (D), lysine (K) or glutamine (Q), serine (S) or asparagine (N);

Xaa4 is cysteine (C) or isoleucine (I);

Xaa5 is isoleucine (I), leucine (L) or valine (V) or an equivalent apolar aliphatic amino acid;

Xaa6 is glutamine (Q), lysine (K), arginine (R) or aspartic acid (D);

Xaa7 is alanine (A), or phenylalanine (F) or an equivalent apolar amino acid; and Xaa8 is isoleucine (I), leucine (L) or valine (V) or an equivalent apolar aliphatic amino acid.

2. The isolated peptide of claim 1 wherein

Xaa1 is asparagine (N) or glutamine (Q);

Xaa2 is aspartic acid (D) or glutamic acid (E);

Xaa3 is asparagine (N) or glutamic acid (E);

Xaa4 is isoleucine (I) or cysteine (C);

Xaa5 is isoleucine (I);

Xaa6 is aspartic acid (D) or glutamine (Q);

Xaa7 is phenylalanine (F) or alanine (A); and

Xaa8 is isoleucine (I).

3. The isolated peptide according to claim 1, wherein the peptide is selected from the group consisting of i) an amino acid sequence ranging from the valine residue at position 7 to the isoleucine residue at position 17 in SEQ ID NO: 1, ii) an amino acid sequence ranging from the valine residue at position 9 to the leucine residue at position 19 in SEQ ID NO:2, and iii) an amino acid sequence at least 80% identical to the sequence of (i) or (ii).

4. The isolated peptide according to claim 1 comprising the amino acid sequence of formula (II):

Yaa1-Yaa2-Yaa3-Yaa4-Yaa5-Valine-Xaa1-Xaa2-Glycine-Leucine-Xaa3-Xaa-4-Xaa5-Xaa6-Xaa7-Xaa8-Yaa6-Yaa7-Yaa8, wherein Xaa1- Xaa2 Xaa3-Xaa4- Xaa5-Xaa6-Xaa7-Xaa8 are as defined in claim 1, Yaa1is aspartic acid (D), glutamic acid (E), or an equivalent acidic amino acid, Yaa2 is glutamine (Q) or lysine (K), Yaa3 is alanine (A), leucine (L) or tyrosine (Y), Yaa4 is glutamic acid (E), tyrosine (Y) or arginine (R), Yaa5 is asparagine (N), histidine (H) or leucine (L), Yaa6 is glutamine (Q), lysine (K), or arginine (R), Yaa7 is lysine (K), alanine (A) or glutamic acid (E), and Yaa8 is asparagine (N), glutamic acid (E) or serine (S).

5. The isolated peptide of claim 1, wherein said isolated peptide is linked to at least one cell-penetrating peptide.

6. A pharmaceutical composition comprising a peptide according to claim 1, and one or more pharmaceutically acceptable excipients.

7. The isolated peptide as defined in claim 1, wherein said peptide is a modified peptide.

8. The isolated peptide according to claim 3, wherein the amino acid sequence of (iii) is an amino acid sequence at least 80% identical to the sequence of (i) or (ii).

9. The isolated peptide according to claim 4, wherein the peptide is selected from the group consisting of i) the amino acid sequence consisting of MDKLELVNDGLNIIDFIQKNQKEIQKTYGRS-SIQQPSIKD (SEQ ID NO: 1);

ii) an amino acid sequence ranging from the leucine residue at position 6 to the aspartic acid residue at position 40 in SEQ ID NO:1;

iii) an amino acid sequence ranging from the leucine residue at position 11 to the aspartic acid residue at position 40 in SEQ ID NO:1;

iv) an amino acid sequence ranging from the methionine residue at position 1 to the asparagine residue at position 20 in SEQ ID NO:1;

v) an amino acid sequence ranging from asparagine residue at position 20 to the glutamine residue at position 35 in SEQ ID NO:1;

vi) the amino acid sequence consisting of MAEEQAYHVSKGLECLKALRENPPDIEEIQEVSSLRDQTC (SEQ ID NO: 2);

vii) an amino acid sequence ranging from the methionine residue at position 1to the asparagine residue at position 22 in SEQ ID NO:2;

viii) the amino acid sequence consisting of DQAENVQEGLECIQAIQKN (SEQ ID NO: 3);

ix) the amino acids sequence consisting of MAEEQARHVKNGLECIRALKAEPIGSLAIEEAMAAWSEIS (SEQ ID NO: 4);

x) an amino acid sequence ranging from the valine residue at position 9 to the leucine residue at position 19 in SEQ ID NO:4; and xi) an amino acid sequence at least 80% identical to the sequence of one of (i) to (x).

10. The isolated peptide according to claim 9, wherein the amino acid sequence of (xi) is an amino acid sequence at least 80% identical to the sequence of one of (i) to (x).

11. A method for producing a peptide as defined in claim 1, wherein said method comprises the steps of:

a) culturing a recombinant cell comprising a recombinant vector comprising a polynucleotide comprising of a nucleic acid encoding a peptide as defined in claim 1 in conditions allowing the expression of the peptide;

b) optionally, purifying the peptide obtained at step a).

12. The method of claim 11, wherein the polynucleotide consists of the nucleic acid encoding the peptide as defined in claim 1.

13. A method for treating a Paramyxovirinae infection comprising a step of administering at least one isolated peptide as defined in claim 1, wherein said Paramyxovirinae infection is selected from the group consisting of Rubulavirus infection, Avulavirus infection, Henipavirus infection, Henipavirus-like infection, Morbillivirus infection, Morbillivirus-like (TPMV-like viruses) infection, Respirovirus infection and Ferlavirus infection.

14. The method for treating a Paramyxovirinae infection as defined in claim 13, wherein said Avulavirus infection is an infection with the Newcastle disease virus;

said Henipavirus infection is an infection with the Nipah virus (NiV) or with the Hendra virus (HeV);

said Morbillivirus infection is an infection with the Measles virus (MeV), the Rinderpest virus, the Canine distemper virus, the phocine distemper virus or the Ovine rinderpest virus;

said TPMV-like virus infection is an infection with the Tupaia paramyxovirus, the Mossman virus, the Nariva virus or the Salem virus;

said Ferlavirus infection is an infection with the Fer-de-Lance virus;

said Rubulavirus infection is an infection with the Mumps virus, the parainfluenza type 2, 4 viruses, the Achimota virus 1 and2, the Simian parainfluenza virus 5, the Menangle virus, the Tioman virus, or the Tuhokovirus 1, 2 and 3; and said Respirovirus infection is an infection with the Sendai virus or the human parainfluenza viruses 1 and 3.

15. The method as defined in claim 13, wherein said isolated peptide is linked to at least one cell-penetrating peptide.

16. The method as defined in claim 13, wherein said isolated peptide is a modified peptide.

* * * * *

SEQUENCE LISTING

<160> NUMBER OF SEQ ID NOS: 44

<210> SEQ ID NO 1
<211> LENGTH: 40
<212> TYPE: PRT
<213> ORGANISM: Artificial
<220> FEATURE:
<223> OTHER INFORMATION: P1-40 Nipah

<400> SEQUENCE: 1

```
Met Asp Lys Leu Glu Leu Val Asn Asp Gly Leu Asn Ile Ile Asp Phe
1               5                   10                  15

Ile Gln Lys Asn Gln Lys Glu Ile Gln Lys Thr Tyr Gly Arg Ser Ser
            20                  25                  30

Ile Gln Gln Pro Ser Ile Lys Asp
        35                  40
```

<210> SEQ ID NO 2
<211> LENGTH: 40
<212> TYPE: PRT
<213> ORGANISM: Artificial
<220> FEATURE:
<223> OTHER INFORMATION: P1-40 CDV

<400> SEQUENCE: 2

```
Met Ala Glu Glu Gln Ala Tyr His Val Ser Lys Gly Leu Glu Cys Leu
1               5                   10                  15

Lys Ala Leu Arg Glu Asn Pro Pro Asp Ile Glu Glu Ile Gln Glu Val
            20                  25                  30

Ser Ser Leu Arg Asp Gln Thr Cys
        35                  40
```

<210> SEQ ID NO 3
<211> LENGTH: 19
<212> TYPE: PRT
<213> ORGANISM: Artificial
<220> FEATURE:
<223> OTHER INFORMATION: consensus peptide

<400> SEQUENCE: 3

```
Asp Gln Ala Glu Asn Val Gln Glu Gly Leu Glu Cys Ile Gln Ala Ile
1               5                   10                  15

Gln Lys Asn
```

<210> SEQ ID NO 4
<211> LENGTH: 40
<212> TYPE: PRT
<213> ORGANISM: Artificial
<220> FEATURE:
<223> OTHER INFORMATION: P1-40 MeV

<400> SEQUENCE: 4

```
Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Ile Glu Glu Ala
            20                  25                  30

Met Ala Ala Trp Ser Glu Ile Ser
        35                  40
```

<210> SEQ ID NO 5
<211> LENGTH: 9
<212> TYPE: PRT
<213> ORGANISM: Artificial
<220> FEATURE:
<223> OTHER INFORMATION: TAT peptide 2

<400> SEQUENCE: 5

```
Arg Lys Lys Arg Arg Gln Arg Arg Arg
1               5
```

<210> SEQ ID NO 6
<211> LENGTH: 11
<212> TYPE: PRT
<213> ORGANISM: Artificial
<220> FEATURE:
<223> OTHER INFORMATION: Tat peptide

<400> SEQUENCE: 6

```
Tyr Gly Arg Lys Lys Arg Arg Gln Arg Arg Arg
1               5                   10
```

<210> SEQ ID NO 7
<211> LENGTH: 9
<212> TYPE: PRT
<213> ORGANISM: Artificial
<220> FEATURE:
<223> OTHER INFORMATION: Polyarginine peptide R9

<400> SEQUENCE: 7

```
Arg Arg Arg Arg Arg Arg Arg Arg Arg
1               5
```

<210> SEQ ID NO 8
<211> LENGTH: 11
<212> TYPE: PRT
<213> ORGANISM: Artificial
<220> FEATURE:
<223> OTHER INFORMATION: Polyarginine peptide R11

<400> SEQUENCE: 8

```
Arg Arg Arg Arg Arg Arg Arg Arg Arg Arg Arg
1               5                   10
```

<210> SEQ ID NO 9
<211> LENGTH: 32
<212> TYPE: PRT
<213> ORGANISM: Artificial
<220> FEATURE:
<223> OTHER INFORMATION: HA2-R9 peptide

<400> SEQUENCE: 9

```
Gly Leu Phe Glu Ala Ile Glu Gly Phe Ile Glu Asn Gly Trp Glu Gly
1               5                   10                  15

Met Ile Asp Gly Trp Tyr Gly Arg Arg Arg Arg Arg Arg Arg Arg Arg
            20                  25                  30
```

<210> SEQ ID NO 10
<211> LENGTH: 16
<212> TYPE: PRT
<213> ORGANISM: Artificial
<220> FEATURE:
<223> OTHER INFORMATION: Penetratin peptide

<400> SEQUENCE: 10

```
Arg Gln Ile Lys Ile Trp Phe Gln Asn Arg Arg Met Lys Trp Lys Lys
1               5                   10                  15
```

<210> SEQ ID NO 11
<211> LENGTH: 27
<212> TYPE: PRT
<213> ORGANISM: Artificial
<220> FEATURE:
<223> OTHER INFORMATION: Transportan peptide

<400> SEQUENCE: 11

```
Gly Trp Thr Leu Asn Ser Ala Gly Tyr Leu Leu Gly Lys Ile Asn Leu
1               5                   10                  15
```

Lys Ala Leu Ala Ala Leu Ala Lys Lys Ile Leu
20 25

<210> SEQ ID NO 12
<211> LENGTH: 33
<212> TYPE: PRT
<213> ORGANISM: Artificial
<220> FEATURE:
<223> OTHER INFORMATION: Maurocalcine peptide

<400> SEQUENCE: 12

Gly Asp Cys Leu Pro His Leu Lys Leu Cys Lys Glu Asn Lys Asp Cys
1 5 10 15

Cys Ser Lys Lys Cys Lys Arg Arg Gly Thr Asn Ile Glu Lys Arg Cys
20 25 30

Arg

<210> SEQ ID NO 13
<211> LENGTH: 10
<212> TYPE: PRT
<213> ORGANISM: Artificial
<220> FEATURE:
<223> OTHER INFORMATION: decalysine peptide

<400> SEQUENCE: 13

Lys Lys Lys Lys Lys Lys Lys Lys Lys Lys
1 5 10

<210> SEQ ID NO 14
<211> LENGTH: 11
<212> TYPE: PRT
<213> ORGANISM: Artificial
<220> FEATURE:
<223> OTHER INFORMATION: HIV-Tat derived PTD4 peptide

<400> SEQUENCE: 14

Tyr Ala Arg Ala Ala Ala Arg Gln Ala Arg Ala
1 5 10

<210> SEQ ID NO 15
<211> LENGTH: 12
<212> TYPE: PRT
<213> ORGANISM: Artificial
<220> FEATURE:
<223> OTHER INFORMATION: Hepatitis B virus Translocation Motif (PTM) peptide

<400> SEQUENCE: 15

Pro Leu Ser Ser Ile Phe Ser Arg Ile Gly Asp Pro
1 5 10

<210> SEQ ID NO 16
<211> LENGTH: 28
<212> TYPE: PRT
<213> ORGANISM: Artificial
<220> FEATURE:
<223> OTHER INFORMATION: mPrP1-28 peptide

<400> SEQUENCE: 16

Met Ala Asn Leu Gly Tyr Trp Leu Leu Ala Leu Phe Val Thr Met Trp
1 5 10 15

Thr Asp Val Gly Leu Cys Lys Lys Arg Pro Lys Pro
20 25

```
<210> SEQ ID NO 17
<211> LENGTH: 35
<212> TYPE: PRT
<213> ORGANISM: Artificial
<220> FEATURE:
<223> OTHER INFORMATION: POD peptide

<400> SEQUENCE: 17

Gly Gly Gly Ala Arg Lys Lys Ala Ala Lys Ala Ala Arg Lys Lys Ala
1               5                   10                  15

Ala Lys Ala Ala Arg Lys Lys Ala Ala Lys Ala Ala Arg Lys Lys Ala
            20                  25                  30

Ala Lys Ala
        35


<210> SEQ ID NO 18
<211> LENGTH: 19
<212> TYPE: PRT
<213> ORGANISM: Artificial
<220> FEATURE:
<223> OTHER INFORMATION: pVEC peptide

<400> SEQUENCE: 18

Leu Leu Ile Ile Leu Arg Arg Arg Arg Ile Arg Lys Gln Ala His Ala
1               5                   10                  15

His Ser Lys


<210> SEQ ID NO 19
<211> LENGTH: 23
<212> TYPE: PRT
<213> ORGANISM: Artificial
<220> FEATURE:
<223> OTHER INFORMATION: EB1 peptide

<400> SEQUENCE: 19

Leu Ile Arg Leu Trp Ser His Leu Ile His Ile Trp Phe Gln Asn Arg
1               5                   10                  15

Arg Leu Lys Trp Lys Lys Lys
            20


<210> SEQ ID NO 20
<211> LENGTH: 22
<212> TYPE: PRT
<213> ORGANISM: Artificial
<220> FEATURE:
<223> OTHER INFORMATION: Rath peptide

<400> SEQUENCE: 20

Thr Pro Trp Trp Arg Leu Trp Thr Lys Trp His His Lys Arg Arg Asp
1               5                   10                  15

Leu Pro Arg Lys Pro Glu
            20


<210> SEQ ID NO 21
<211> LENGTH: 20
<212> TYPE: PRT
<213> ORGANISM: Artificial
<220> FEATURE:
<223> OTHER INFORMATION: CADY peptide

<400> SEQUENCE: 21

Gly Leu Trp Arg Ala Leu Trp Arg Leu Leu Arg Ser Leu Trp Arg Leu
1               5                   10                  15

Leu Trp Arg Ala
```

20

<210> SEQ ID NO 22
<211> LENGTH: 24
<212> TYPE: PRT
<213> ORGANISM: Artificial
<220> FEATURE:
<223> OTHER INFORMATION: Histatin 5 peptide

<400> SEQUENCE: 22

Asp Ser His Ala Lys Arg His His Gly Tyr Lys Arg Lys Phe His Glu
1               5                   10                  15

Lys His His Ser His Arg Gly Tyr
            20

<210> SEQ ID NO 23
<211> LENGTH: 16
<212> TYPE: PRT
<213> ORGANISM: Artificial
<220> FEATURE:
<223> OTHER INFORMATION: Antp peptide

<400> SEQUENCE: 23

Arg Gln Ile Lys Ile Trp Phe Gln Asn Arg Arg Met Lys Trp Lys Lys
1               5                   10                  15

<210> SEQ ID NO 24
<211> LENGTH: 16
<212> TYPE: PRT
<213> ORGANISM: Artificial
<220> FEATURE:
<223> OTHER INFORMATION: Cyt86-101 peptide

<400> SEQUENCE: 24

Lys Lys Lys Glu Glu Arg Ala Asp Leu Ile Ala Tyr Leu Lys Lys Ala
1               5                   10                  15

<210> SEQ ID NO 25
<211> LENGTH: 12
<212> TYPE: PRT
<213> ORGANISM: Artificial
<220> FEATURE:
<223> OTHER INFORMATION: DPT peptide

<400> SEQUENCE: 25

Val Lys Lys Lys Lys Ile Lys Arg Glu Ile Lys Ile
1               5                   10

<210> SEQ ID NO 26
<211> LENGTH: 120
<212> TYPE: DNA
<213> ORGANISM: Artificial
<220> FEATURE:
<223> OTHER INFORMATION: P40 Nipah nucleotidic sequence

<400> SEQUENCE: 26
atggataaat tggaactagt caatgatggc ctcaatatta ttgactttat tcagaagaac     60
caaaaagaaa tacagaagac atacggacga tcaagtattc aacaacccag catcaaagat    120

<210> SEQ ID NO 27
<211> LENGTH: 120
<212> TYPE: DNA
<213> ORGANISM: Artificial
<220> FEATURE:
<223> OTHER INFORMATION: P40 CDV nucleotidic sequence

<400> SEQUENCE: 27
atggcagagg aacaggccta ccatgtcagc aaagggctgg aatgcctcaa agccctcaga 60
gagaatcctc ctgacattga ggagattcaa gaggtcagca gcctcagaga ccaaacctgc 120

<210> SEQ ID NO 28
<211> LENGTH: 120
<212> TYPE: DNA
<213> ORGANISM: Artificial
<220> FEATURE:
<223> OTHER INFORMATION: P40 MeV nucleotidic sequence

<400> SEQUENCE: 28
atggcagaag agcaggcacg ccatgtcaaa aacggactgg aatgcatccg ggctctcaag 60
gccgagccca tcggctcact ggccatcgag gaagctatgg cagcatggtc agaaatatca 120

<210> SEQ ID NO 29
<211> LENGTH: 17
<212> TYPE: PRT
<213> ORGANISM: Artificial
<220> FEATURE:
<223> OTHER INFORMATION: N189-205 Nipah

<400> SEQUENCE: 29

Ser Glu Thr Arg Arg Trp Ala Lys Tyr Val Gln Gln Lys Arg Val Asn
1 5 10 15

Pro

<210> SEQ ID NO 30
<211> LENGTH: 17
<212> TYPE: PRT
<213> ORGANISM: Artificial
<220> FEATURE:
<223> OTHER INFORMATION: N191-207 Mev

<400> SEQUENCE: 30

Ser Glu Leu Arg Arg Trp Ile Lys Tyr Thr Gln Gln Arg Arg Val Val
1 5 10 15

Gly

<210> SEQ ID NO 31
<211> LENGTH: 17
<212> TYPE: PRT
<213> ORGANISM: Artificial
<220> FEATURE:
<223> OTHER INFORMATION: N191-207 Muv

<400> SEQUENCE: 31

Ser Ala Asp Arg Arg Phe Ala Lys Tyr Gln Gln Gln Gly Arg Leu Glu
1 5 10 15

Ala

<210> SEQ ID NO 32
<211> LENGTH: 17
<212> TYPE: PRT
<213> ORGANISM: Artificial
<220> FEATURE:
<223> OTHER INFORMATION: N189-205 NDV

<400> SEQUENCE: 32

Ser Glu Thr Arg Arg Ile Asn Lys Tyr Met Gln Gln Gly Arg Val Gln
1 5 10 15

Lys

<210> SEQ ID NO 33
<211> LENGTH: 21
<212> TYPE: PRT
<213> ORGANISM: Artificial
<220> FEATURE:
<223> OTHER INFORMATION: N253-273 Nipah

<400> SEQUENCE: 33

Ser Asp Ile Gly Asn Tyr Val Glu Glu Thr Gly Met Ala Gly Phe Phe
1 5 10 15

Ala Thr Ile Arg Phe
20

<210> SEQ ID NO 34
<211> LENGTH: 21
<212> TYPE: PRT
<213> ORGANISM: Artificial
<220> FEATURE:
<223> OTHER INFORMATION: N253-273 Mev

<400> SEQUENCE: 34

Cys Asp Ile Asp Thr Tyr Ile Val Glu Ala Gly Leu Ala Ser Phe Ile
1 5 10 15

Leu Thr Ile Lys Phe
20

<210> SEQ ID NO 35
<211> LENGTH: 21
<212> TYPE: PRT
<213> ORGANISM: Artificial
<220> FEATURE:
<223> OTHER INFORMATION: N253-273 Muv

<400> SEQUENCE: 35

Gly Asp Ile Gly Lys Tyr Ile Glu Asn Ser Gly Leu Thr Ala Phe Phe
1 5 10 15

Leu Thr Leu Lys Tyr
20

<210> SEQ ID NO 36
<211> LENGTH: 21
<212> TYPE: PRT
<213> ORGANISM: Artificial
<220> FEATURE:
<223> OTHER INFORMATION: N251-271 NDV

<400> SEQUENCE: 36

Gly Asp Val Asp Ser Tyr Ile Arg Asn Thr Gly Leu Thr Ala Phe Phe
1 5 10 15

Leu Thr Leu Lys Tyr
20

<210> SEQ ID NO 37
<211> LENGTH: 17
<212> TYPE: PRT
<213> ORGANISM: Artificial Sequence
<220> FEATURE:
<223> OTHER INFORMATION: NiV 189-205

<400> SEQUENCE: 37

Ser Glu Thr Arg Arg Trp Ala Lys Tyr Val Gln Gln Lys Arg Val Asn
1 5 10 15

Pro

<210> SEQ ID NO 38
<211> LENGTH: 17
<212> TYPE: PRT
<213> ORGANISM: Artificial Sequence
<220> FEATURE:
<223> OTHER INFORMATION: MeV 191-207

<400> SEQUENCE: 38

Ser Glu Leu Arg Arg Trp Ile Lys Tyr Thr Gln Gln Arg Arg Val Val
1 5 10 15

Gly

<210> SEQ ID NO 39
<211> LENGTH: 17
<212> TYPE: PRT
<213> ORGANISM: Artificial Sequence
<220> FEATURE:
<223> OTHER INFORMATION: MuV 191-207

<400> SEQUENCE: 39

Ser Ala Asp Arg Arg Phe Ala Lys Tyr Gln Gln Gln Gly Arg Leu Glu
1 5 10 15

Ala

<210> SEQ ID NO 40
<211> LENGTH: 17
<212> TYPE: PRT
<213> ORGANISM: Artificial Sequence
<220> FEATURE:
<223> OTHER INFORMATION: NDV 189-205

<400> SEQUENCE: 40

Ser Glu Thr Arg Arg Ile Asn Lys Tyr Met Gln Gln Gly Arg Val Gln
1 5 10 15

Lys

<210> SEQ ID NO 41
<211> LENGTH: 21
<212> TYPE: PRT
<213> ORGANISM: Artificial Sequence
<220> FEATURE:
<223> OTHER INFORMATION: NiV 253-273

<400> SEQUENCE: 41

Ser Asp Ile Gly Asn Tyr Val Glu Glu Thr Gly Met Ala Gly Phe Phe
1 5 10 15

Ala Thr Ile Arg Phe
20

<210> SEQ ID NO 42
<211> LENGTH: 21
<212> TYPE: PRT
<213> ORGANISM: Artificial Sequence
<220> FEATURE:
<223> OTHER INFORMATION: MeV 253-273

<400> SEQUENCE: 42

Cys Asp Ile Asp Thr Tyr Ile Val Glu Ala Gly Leu Ala Ser Phe Ile
1 5 10 15

Leu Thr Ile Lys Phe
20

-continued

```
<210> SEQ ID NO 43
<211> LENGTH: 21
<212> TYPE: PRT
<213> ORGANISM: Artificial Sequence
<220> FEATURE:
<223> OTHER INFORMATION: MuV 253-273

<400> SEQUENCE: 43

Gly Asp Ile Gly Lys Tyr Ile Glu Asn Ser Gly Leu Thr Ala Phe Phe
1               5                   10                  15

Leu Thr Leu Lys Tyr
            20


<210> SEQ ID NO 44
<211> LENGTH: 21
<212> TYPE: PRT
<213> ORGANISM: Artificial Sequence
<220> FEATURE:
<223> OTHER INFORMATION: NDV 251-271

<400> SEQUENCE: 44

Gly Asp Val Asp Ser Tyr Ile Arg Asn Thr Gly Leu Thr Ala Phe Phe
1               5                   10                  15

Leu Thr Leu Lys Tyr
            20
```